United States Patent
Fu et al.

(10) Patent No.: US 11,766,532 B2
(45) Date of Patent: Sep. 26, 2023

(54) AUTO-FIT MASK

(71) Applicant: ResMed Pty Ltd, Bella Vista (AU)

(72) Inventors: Timothy Tsun-Fai Fu, Sydney (AU); Sakeena De Souza, Sydney (AU)

(73) Assignee: ResMed Pty Ltd

( * ) Notice: Subject to any disclaimer, the term of this patent is extended or adjusted under 35 U.S.C. 154(b) by 0 days.

(21) Appl. No.: 17/825,241

(22) Filed: May 26, 2022

(65) Prior Publication Data

US 2022/0387740 A1 Dec. 8, 2022

Related U.S. Application Data

(63) Continuation of application No. 15/313,788, filed as application No. PCT/AU2015/050352 on Jun. 24, 2015, now abandoned.
(Continued)

(51) Int. Cl.
*A61M 16/00* (2006.01)
*A61M 16/06* (2006.01)
(Continued)

(52) U.S. Cl.
CPC ...... *A61M 16/024* (2017.08); *A61M 16/0051* (2013.01); *A61M 16/0066* (2013.01);
(Continued)

(58) Field of Classification Search
CPC .......... A61M 16/0051; A61M 16/0066; A61M 16/024; A61M 16/026; A61M 16/0605;
(Continued)

(56) References Cited

U.S. PATENT DOCUMENTS

| 4,782,832 A | 11/1988 | Trimble et al. |
| 4,944,310 A | 7/1990 | Sullivan |

(Continued)

FOREIGN PATENT DOCUMENTS

| WO | 19980004310 A1 | 2/1998 |
| WO | 19980034665 A1 | 8/1998 |

(Continued)

OTHER PUBLICATIONS

The International Search report and The Written Opinion for International Patent Application No. PCT/AU2015/050352 dated Sep. 24, 2015.

*Primary Examiner* — Colin W Stuart
*Assistant Examiner* — Matthew D Ziegler
(74) *Attorney, Agent, or Firm* — Botos Churchill IP Law LLP

(57) ABSTRACT

Devices, systems, and methods for detecting a sealing condition between a patient interface and a patient, and adjusting the patient interface to maintain the patient interface in sealing contact with the patient. The patient interface may include a sealing structure to form a seal on the patient, and a positioning structure to secure the sealing structure to the patient. The patient interface may include a sensor coupled to the sealing structure. A processor determines the sealing condition between the sealing structure and the patient based on a signal from the sensor, and adjusts at least one of the sealing structure and the positioning structure to maintain the sealing structure in sealing contact with the patient. A prediction system predicts a leak between the sealing structure and the patient based on the sensor signal. A learning system learns how to fit the sealing structure to the patient to form a seal.

29 Claims, 34 Drawing Sheets

Related U.S. Application Data

(60) Provisional application No. 62/018,025, filed on Jun. 27, 2014.

(51) Int. Cl.
  *A61M 16/16* (2006.01)
  *A61M 16/10* (2006.01)

(52) U.S. Cl.
  CPC ...... *A61M 16/026* (2017.08); *A61M 16/0605* (2014.02); *A61M 16/0616* (2014.02); *A61M 16/0633* (2014.02); *A61M 16/0683* (2013.01); *A61M 16/16* (2013.01); *A61M 16/107* (2014.02); *A61M 2016/003* (2013.01); *A61M 2016/0027* (2013.01); *A61M 2016/0661* (2013.01); *A61M 2205/0283* (2013.01); *A61M 2205/0288* (2013.01); *A61M 2205/0294* (2013.01); *A61M 2205/13* (2013.01); *A61M 2205/15* (2013.01); *A61M 2205/332* (2013.01); *A61M 2205/3303* (2013.01); *A61M 2205/3306* (2013.01); *A61M 2205/3317* (2013.01); *A61M 2205/3331* (2013.01); *A61M 2205/3334* (2013.01); *A61M 2205/3368* (2013.01); *A61M 2205/3375* (2013.01); *A61M 2205/3569* (2013.01); *A61M 2205/3592* (2013.01); *A61M 2205/502* (2013.01); *A61M 2205/52* (2013.01); *A61M 2205/581* (2013.01); *A61M 2205/583* (2013.01); *A61M 2205/8206* (2013.01); *A61M 2230/08* (2013.01); *A61M 2230/201* (2013.01); *A61M 2230/205* (2013.01); *A61M 2230/60* (2013.01); *A61M 2230/62* (2013.01)

(58) Field of Classification Search
  CPC .......... A61M 16/0616; A61M 16/0633; A61M 16/0683; A61M 16/107; A61M 16/16; A61M 16/00; A61M 16/0003; A61M 16/021; A61M 16/022; A61M 16/06; A61M 2016/0027; A61M 2016/003; A61M 2016/0661; A61M 2205/0283; A61M 2205/0288; A61M 2205/0294; A61M 2205/13; A61M 2205/15; A61M 2205/3303; A61M 2205/3306; A61M 2205/3317; A61M 2205/332; A61M 2205/3331; A61M 2205/3334; A61M 2205/3368; A61M 2205/3375; A61M 2205/3569; A61M 2205/3592; A61M 2205/502; A61M 2205/52; A61M 2205/581; A61M 2205/583; A61M 2205/8206; A61M 2205/0272; A61M 2205/0227; A61M 2205/33; A61M 2205/50; A61M 2205/82; A61M 2205/8262; A61M 2230/08; A61M 2230/201; A61M 2230/205; A61M 2230/60; A61M 2230/62; A61M 2210/06; A61M 2210/0606; A61M 2210/0625; A62B 9/006

See application file for complete search history.

(56) References Cited

U.S. PATENT DOCUMENTS

| | | | |
|---|---|---|---|
| 5,503,146 | A | 4/1996 | Froehlich et al. |
| 5,503,147 | A | 4/1996 | Bertheau |
| 6,240,921 | B1 | 6/2001 | Brydon |
| 6,532,959 | B1 | 3/2003 | Berthon-Jones |
| 6,581,594 | B1 | 6/2003 | Drew et al. |
| 6,826,968 | B2 * | 12/2004 | Manaresi ................ G01L 1/146 |
| | | | 73/862.626 |
| 8,162,857 | B2 | 4/2012 | Lanfermann et al. |
| 8,276,588 | B1 | 10/2012 | Connor |
| 8,573,199 | B2 | 11/2013 | King et al. |
| 9,888,858 | B2 * | 2/2018 | Farrugia ............. A61B 5/4836 |
| 10,046,131 | B2 | 8/2018 | Hendriks et al. |
| 10,228,801 | B2 * | 3/2019 | Robucci ................ G06F 3/0346 |
| 10,376,155 | B2 * | 8/2019 | Yang ....................... G01L 1/146 |
| 2004/0163648 | A1 | 8/2004 | Burton |
| 2006/0174883 | A1 | 8/2006 | Aylsworth |
| 2008/0083412 | A1 | 4/2008 | Henry et al. |
| 2008/0192459 | A1 | 8/2008 | Kwok |
| 2008/0202528 | A1 | 8/2008 | Carter |
| 2009/0044808 | A1 | 2/2009 | Guney et al. |
| 2009/0050156 | A1 | 2/2009 | Ng et al. |
| 2010/0000534 | A1 | 1/2010 | Kooij et al. |
| 2011/0220112 | A1 | 9/2011 | Conner |
| 2012/0190998 | A1 | 7/2012 | Armitstead |
| 2013/0032148 | A1 | 2/2013 | Neely |
| 2013/0118500 | A1 | 5/2013 | Stevens et al. |
| 2014/0069428 | A1 | 3/2014 | Sears et al. |
| 2014/0158136 | A1 * | 6/2014 | Romagnoli ....... A61M 16/0683 |
| | | | 128/206.24 |

FOREIGN PATENT DOCUMENTS

| | | | |
|---|---|---|---|
| WO | 0078381 | A1 | 12/2000 |
| WO | 0143804 | A1 | 6/2001 |
| WO | 02056818 | A2 | 7/2002 |
| WO | 2004041342 | A1 | 5/2004 |
| WO | 2004073778 | A1 | 9/2004 |
| WO | 2005063328 | A1 | 7/2005 |
| WO | 2006074513 | A1 | 7/2006 |
| WO | 2006130903 | A1 | 12/2006 |
| WO | 2009052560 | A1 | 4/2009 |
| WO | 2010135785 | A1 | 12/2010 |
| WO | 2011073814 | A1 | 6/2011 |
| WO | 2013050911 | A1 | 4/2013 |
| WO | 2013067582 | A1 | 5/2013 |
| WO | 2013183018 | A1 | 12/2013 |
| WO | 2014024086 | A1 | 2/2014 |
| WO | 2014175752 | A2 | 10/2014 |
| WO | 2015002652 | A1 | 1/2015 |
| WO | 2015022595 | A1 | 2/2015 |
| WO | 2015128173 | A1 | 9/2015 |

* cited by examiner

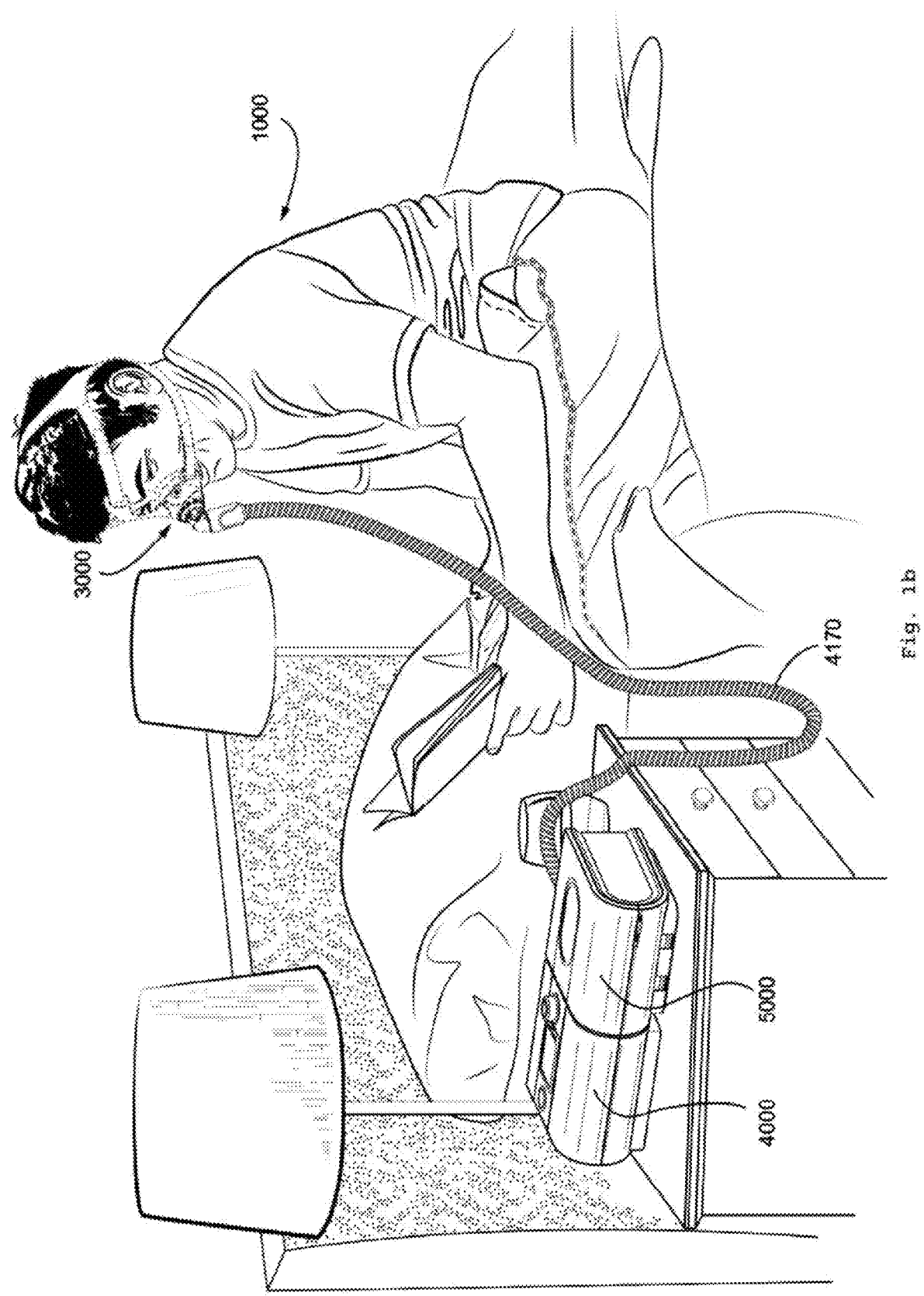

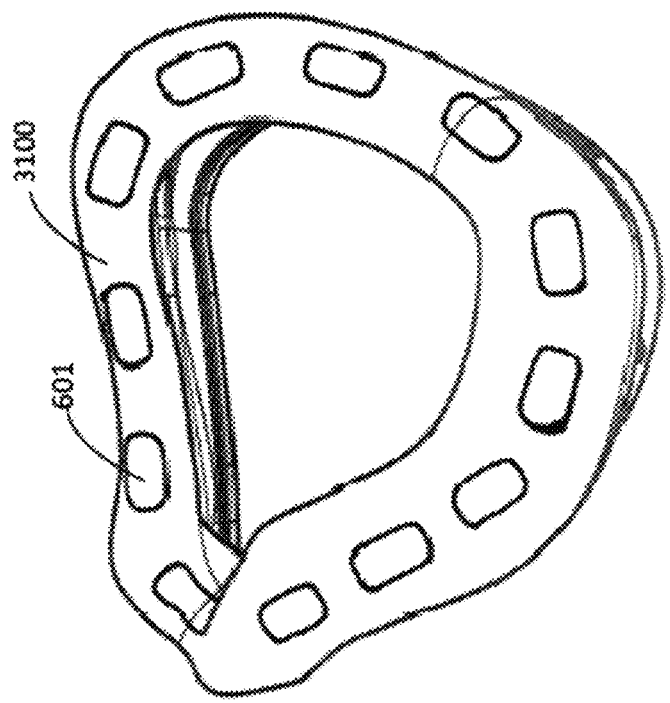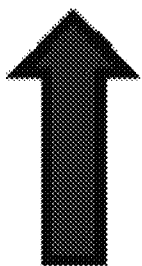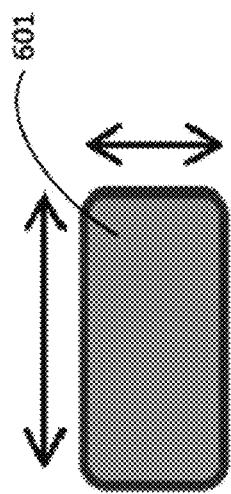
Fig. 6

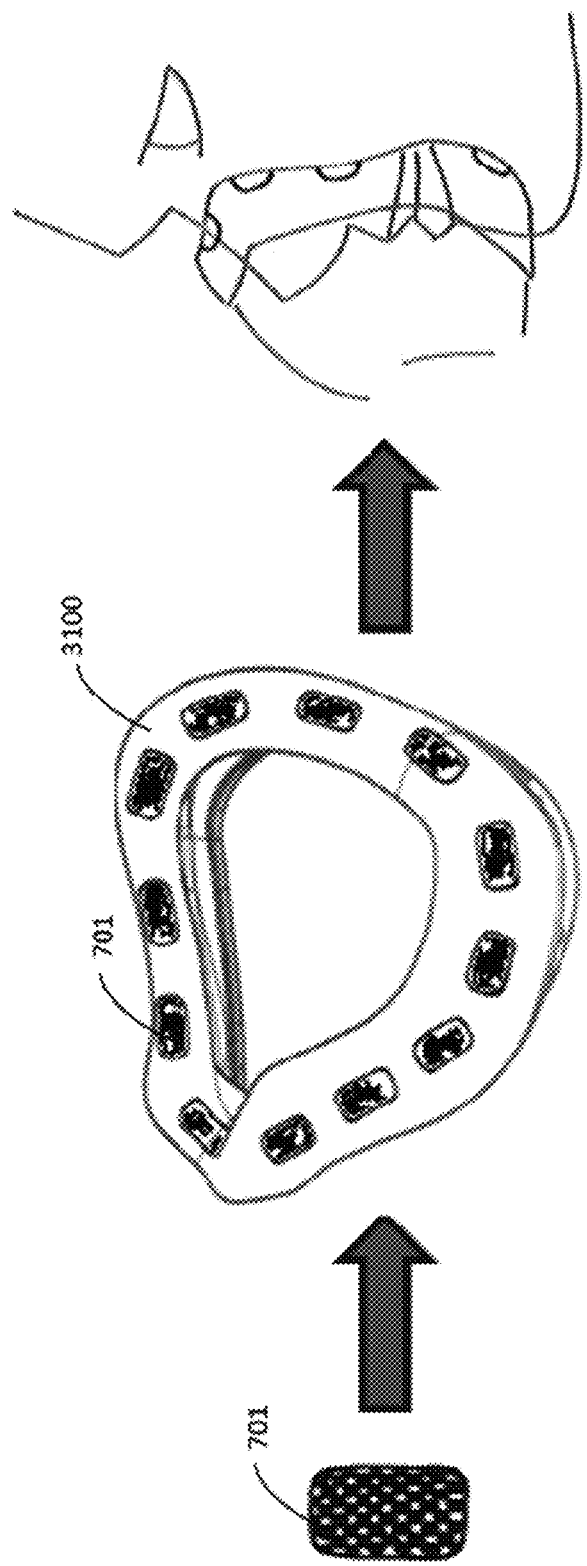

AUTO-FIT MASK

1 CROSS-REFERENCE TO RELATED APPLICATIONS

The present application is a continuation of U.S. application Ser. No. 15/313,788, filed Nov. 23, 2016, which application is a national phase entry under 35 U.S.C. § 371 of International Application No. PCT/AU2015/050352, filed Jun. 24, 2015, published in English, which claims the priority from U.S. Provisional Patent Application No. 62/018,025, filed on Jun. 27, 2014, all of which are incorporated herein by reference.

2 BACKGROUND OF THE TECHNOLOGY

2.1 Field of the Technology

The present technology relates to a patient interface designed for respiratory-related therapies. In particular, the present technology relates to an auto-fit patient interface, such as a mask, that fits a user automatically with minimal or no user interaction.

2.2 Description of the Related Art 2.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "Respiratory Physiology", by John B. West, Lippincott Williams & Wilkins, 9th edition published 2011.

A range of respiratory disorders exist. Certain disorders may be characterised by particular events, e.g. apneas, hypopneas, and hyperpneas.

Obstructive Sleep Apnea (OSA), a form of Sleep Disordered Breathing (SDB), is characterized by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapy

Nasal Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall. Treatment of OSA by nasal CPAP therapy may be voluntary, and hence patients may elect not to comply with therapy if they find devices used to provide such therapy one or more of uncomfortable, difficult to use, expensive or aesthetically unappealing.

Non-invasive ventilation (NIV) provides ventilatory support to a patient through the upper airways to assist the patient in taking a full breath and/or maintain adequate oxygen levels in the body by doing some or all of the work of breathing. The ventilatory support is provided via a patient interface. NIV has been used to treat CSR, OHS, COPD, MD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.3 Diagnosis and Treatment Systems

These therapies may be provided by a treatment system or device. Systems and devices may also be used to diagnose a condition without treating it.

A treatment system may comprise a Respiratory Pressure Therapy Device (RPT device), an air circuit, a humidifier, a patient interface, and data management.

Another form of treatment system is a mandibular repositioning device.

2.2.3.1 Patient Interface

A patient interface may be used to interface respiratory equipment to its user, for example by providing a flow of air. The flow of air may be provided via a mask to the nose and/or mouth, a tube to the mouth or a tracheostomy tube to the trachea of the user. Depending upon the therapy to be applied, the patient interface may form a seal, e.g. with a face region of the patient, to facilitate the delivery of gas at a pressure at sufficient variance with ambient pressure to effect therapy, e.g. a positive pressure of about 10 cmH2O. For other forms of therapy, such as the delivery of oxygen, the patient interface may not include a seal sufficient to facilitate delivery to the airways of a supply of gas at a positive pressure of about 10 cmH2O.

The design of a patient interface presents a number of challenges. The face has a complex three-dimensional shape. The size and shape of noses varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. For example, masks designed solely for aviators, mask designed as part of personal protection equipment (e.g. filter masks), SCUBA masks, or for the administration of anaesthetics may be tolerable for their original application, but nevertheless be undesirably uncomfortable to be worn for extended periods of time, e.g. several hours. This discomfort may lead to a reduction in patient compliance with therapy. This is even more so if the mask is to be worn during sleep.

Nasal CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g. difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of nasal CPAP during sleep form a distinct field.

Currently, to detect if a patient interface is properly placed over the patient's face, one approach is to use a flow generator to identify leaks. This approach has several flaws, such as latency and inability to identify the exact position of leakage. As a result, this approach cannot provide explicit instructions to the patient regarding how to adjust the patient interface to stop leakage. This approach also cannot automatically adjust the patient interface to stop the leakage without patient involvement.

Currently, to obtain patient interface stability or to obtain an optimum seal, one approach is to require the patient to adjust headgear tension or adjust the position of the patient interface relative to their airways. As a result, when the patient is asleep, adjustment to the patient interface cannot be performed.

In view of the foregoing, it will be appreciated that there may be a need for improved techniques to detect leakage between the patient interface and human skin. There may also be a need for improved techniques to automatically fit the patient interface to human skin with minimal or no human interaction. Seal-forming portion Patient interfaces may include a seal-forming portion. Since it is in direct contact with the patient's face, the shape and configuration of the seal-forming portion can have a direct impact the effectiveness and comfort of the patient interface.

A patient interface may be partly characterised according to the design intent of where the seal-forming portion is to engage with the face in use. In one form of patient interface, a seal-forming portion may comprise two sub-portions to engage with respective left and right nares. In one form of patient interface, a seal-forming portion may comprise a single element that surrounds both nares in use. Such single element may be designed to for example overlay an upper lip region and a nasal bridge region of a face. In one form of patient interface a seal-forming portion may comprise an element that surrounds a mouth region in use, e.g. by forming a seal on a lower lip region of a face. In one form of patient interface, a seal-forming portion may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming portion that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming portions may be designed for mass manufacture such that one design fit and be comfortable and effective for a wide range of different face shapes and sizes. To the extent to which there is a mismatch between the shape of the patient's face, and the seal-forming portion of the mass-manufactured patient interface, one or both must adapt in order for a seal to form.

One type of seal-forming portion extends around the periphery of the patient interface, and is intended to seal against the user's face when force is applied to the patient interface with the seal-forming portion in confronting engagement with the user's face. The seal-forming portion may include an air or fluid filled cushion, or a moulded or formed surface of a resilient seal element made of an elastomer such as a rubber. With this type of seal-forming portion, if the fit is not adequate, there will be gaps between the seal-forming portion and the face, and additional force will be required to force the patient interface against the face in order to achieve a seal.

Another type of seal-forming portion incorporates a flap seal of thin material so positioned about the periphery of the mask so as to provide a self-sealing action against the face of the user when positive pressure is applied within the mask. Like the previous style of seal forming portion, if the match between the face and the mask is not good, additional force may be required to effect a seal, or the mask may unintentionally leak. Furthermore, if the shape of the seal-forming portion does not match that of the patient, it may crease or buckle in use, giving rise to unintentional leaks.

Another type of seal-forming portion may comprise a friction-fit element, e.g. for insertion into a naris, however some patients find these uncomfortable.

Another form of seal-forming portion may use adhesive to effect a seal. Some patients may find it inconvenient to constantly apply and remove an adhesive to their face.

A range of patient interface seal-forming portion technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT nasal pillows mask, SWIFT II nasal pillows mask, SWIFT LT nasal pillows mask, SWIFT FX nasal pillows mask and LIBERTY full-face mask. The following patent applications, assigned to ResMed Limited, describe nasal pillows masks: International Patent Application WO2004/073,778 (describing amongst other things aspects of ResMed SWIFT nasal pillows), US Patent Application 2009/0044808 (describing amongst other things aspects of ResMed SWIFT LT nasal pillows); International Patent Applications WO 2005/063,328 and WO 2006/130,903 (describing amongst other things aspects of ResMed LIBERTY full-face mask); International Patent Application WO 2009/052,560 (describing amongst other things aspects of ResMed SWIFT FX nasal pillows).

2.2.3.1.1 Positioning and Stabilising

A seal-forming portion of a patient interface used for positive air pressure therapy is subject to the corresponding force of the air pressure to disrupt a seal. Thus a variety of techniques have been used to position the seal-forming portion, and to maintain it in sealing relation with the appropriate portion of the face.

One technique is the use of adhesives. See for example US Patent publication US 2010/0000534. However these may be uncomfortable for some.

Another technique is the use of one or more straps and stabilising harnesses. Many such harnesses suffer from being one or more of ill-fitting, bulky, uncomfortable and awkward to use.

2.2.3.1.2 Vent Technologies

Some forms of patient interface systems may include a vent to allow the washout of exhaled carbon dioxide. The vent may allow a flow of gas from an interior space of the patient interface, e.g. the plenum chamber, to an exterior of the patient interface, e.g. to ambient. The vent may comprise an orifice and gas may flow through the orifice in use of the mask. Many such vents are noisy. Others may block in use and provide insufficient washout. Some vents may be disruptive of the sleep of a bed-partner 1100 of the patient 1000, e.g. through noise or focused airflow.

ResMed Limited has developed a number of improved mask vent technologies. See WO 1998/034,665; WO 2000/078,381; U.S. Pat. No. 6,581,594; US Patent Application; US 2009/0050156; US Patent Application 2009/0044808.

Table of noise of prior masks (ISO 17510-2:2007, 10 cm $H_2O$ pressure at 1 m)

| Mask name | Mask type | A-weighted sound power level dB(A) (uncertainty) | A-weighted sound pressure dB(A) (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage (*) | nasal | 29.5 | 21.5 | 1998 |
| ResMed UltraMirage | nasal | 36 (3) | 28 (3) | 2000 |
| ResMed Mirage Activa | nasal | 32 (3) | 24 (3) | 2002 |
| ResMed Mirage Micro | nasal | 30 (3) | 22 (3) | 2008 |
| ResMed Mirage SoftGel | nasal | 29 (3) | 22 (3) | 2008 |
| ResMed Mirage FX | nasal | 26 (3) | 18 (3) | 2010 |
| ResMed Mirage Swift (*) | nasal pillows | 37 | 29 | 2004 |
| ResMed Mirage Swift II | nasal pillows | 28 (3) | 20 (3) | 2005 |
| ResMed Mirage Swift LT | nasal pillows | 25 (3) | 17 (3) | 2008 |

(* one specimen only, measured using test method specified in ISO3744 in CPAP mode at 10 cm $H_2O$)

Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO3744 at 1 m distance |
| Conversational speech | 60 | 1 m distance |
| Average home | 50 | |
| Quiet library | 40 | |
| Quiet bedroom at night | 30 | |
| Background in TV studio | 20 | |

2.2.3.2 Respiratory Pressure Therapy (RPT) Device

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, including one or more of comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO3744 in CPAP mode at 10 cmH$_2$O).

| RPT Device name | A-weighted sound power level dB(A) | Year (approx.) |
|---|---|---|
| C-Series Tango | 31.9 | 2007 |
| C-Series Tango with Humidifier | 33.1 | 2007 |
| S8 Escape II | 30.5 | 2005 |
| S8 Escape II with H4i Humidifier | 31.1 | 2005 |
| S9 AutoSet | 26.5 | 2010 |
| S9 AutoSet with H5i Humidifier | 28.6 | 2010 |

One known RPT device used for treating sleep disordered breathing is the S9 Sleep Therapy System, manufactured by ResMed. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

2.2.3.3 Humidifier

Delivery of a flow of air without humidification may cause drying of airways. The use of a humidifier with a RPT device and the patient interface produces humidified gas that minimizes drying of the nasal mucosa and increases patient airway comfort. In addition in cooler climates, warm air applied generally to the face area in and about the patient interface is more comfortable than cold air. A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). As a result, a medical humidifier is preferably small for bedside placement, and it is preferably configured to only humidify and/or heat the flow of air delivered to the patient without humidifying and/or heating the patient's surroundings. Room-based systems (e.g. a sauna, an air conditioner, an evaporative cooler), for example, may also humidify air that is breathed in by the patient, however they would also humidify and/or heat the entire room, which may cause discomfort to the occupants. Furthermore medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

3 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

Some versions of the technology may include a patient interface for sealed delivery of a flow of breathable gas to a patient's airway. The patient interface may include a sealing structure to form a seal on the patient's face. The patient interface may include a positioning structure to secure the sealing structure to the patient's face. The patient interface may include a sensor coupled to the sealing structure and configured to generate a sensor signal. The patient interface may include a processor connected with the sensor, the processor configured to determine a sealing condition between the sealing structure and the patient based on the sensor signal, the processor further configured to adjust at least one of the sealing structure and the positioning structure to maintain the sealing structure in sealing contact with the patient.

In some cases, the patient interface may include the processor being configured to adjust at least one of the sealing structure and the positioning structure based on the determined sealing condition. The patient interface may be one of a nasal mask, nasal pillows, a nasal puff, and an oro-nasal mask. The patient interface may include the sensor which may generate a fluctuating sensor signal indicative of an unstable contact between the sealing structure and the patient's face. The patient interface may include the processor being configured to generate a warning signal indicating the determined sealing condition. The patient interface may further include a power source to power at least one of the sealing structure, the positioning structure, the sensor, and the processor.

Optionally in some versions of the technology, the patient interface may include the power being in one of the following forms: a solid state battery, energy harvesting, microturbine, RF, induction coupling, wireless power, and wired power. The power source may be one of a 5V DC battery, a Lithium cell, a button cell, and a power supply of at least 3.0V. The patient interface may further include a display. The display may be any one of a voltmeter, a computer interface, and a serial monitor.

In some versions of the technology, the patient interface may include the processor being any one of an Arduino processor, an Arduino Mega2560 Board, Arduino Uno Board, and Atmega128L. The processor may be configured to control a flow generator to supply the flow of breathable gas to the patient based on the determined sealing condition. The processor may instruct the flow generator to start supplying the flow of breathable gas to the patient when the sealing structure is in sealing contact with the patient. The processor may instruct the flow generator to stop supplying the flow of breathable gas to the patient when the sealing structure is not in sealing contact with the patient.

Optionally, in some versions, the patient interface may further include a high pass filter to filter a frequency oscillation in the sensor signal. The patient interface may include the sealing structure which may include a conductive path transmitting the sensor signal to the processor. The sensor may be one of a capacitive sensor, a resistive sensor, a resistive ink bend sensor, a shear sensor, and a piezoelectric film sensor. The processor may be configured to determine a distance between the sealing structure and the patient's face based on the sensor signal.

In some versions of the technology, the patient interface may further include a plurality of sensors arranged at different locations on the sealing structure to determine proximity between different locations on the sealing structure and the patient's face. The patient interface may include the determined sealing condition which may include any one of (1) an unintentional leak, (2) an adequate contact, and (3) an inadequate contact between the sealing structure and the patient's face.

Some versions of the technology may include a system for predicting an unintentional leak between a patient interface and a patient's face. The system may include a processor configured to receive a sensor signal from a sensor coupled to the patient interface, the processor configured to predict a likelihood of an unintentional leak between the patient interface and the patient's face based on the sensor signal. The likelihood of a seal leak may include one of an imminent leak and a leak during the same therapy session.

Optionally, in some versions, the system may include the sensor signal which may indicate at least one of force, pressure, seal contact pressure, shear, friction, orientation, position, transcutaneous oximetry, and tissue hypoperfusivity. The system may include the processor which may predict the likelihood of an unintentional leak based on the sensor signal and a time element associated with the sensor signal. The processor may be configured to detect an onset of at least one of a pressure sore and patient discomfort. The processor may be configured to adjust the patient interface to prevent the unintentional leak from occurring. The processor may be configured to issue an instruction to tighten a headgear strap of the patient interface.

In some versions, the system may include the processor which may predict the unintentional leak determining a rate of change of a sensor reading, and comparing the rate of change to a predetermined threshold. The processor may determine that an unintentional leak may be likely to occur when the rate of change exceeds the predetermined threshold. The processor may be configured to determine whether a patient is shifting based on an orientation signal obtained from an orientation sensor. The processor may initiate a preventive action which may compensate for orientations known to increase the likelihood of a unintentional leak. The processor may be configured to determine hypoperfusion.

Some versions of the technology may include a system for learning how to fit a patient interface to a patient's face to form a seal. The system may include a memory storing at least one historical setting of a patient interface for fitting the patient interface to the patient's face. The system may include a processor configured to analyze the at least one historical setting, and determine a setting to be applied to the patient interface to form a seal with the patient's face.

Optionally, in some versions, the system may include the historical setting which may be a user preferred setting. The system may include the memory which may be a solid state memory. The historical setting may include a patient interface parameter associated with at least one of a strap length, strap elasticity modulus, force, pressure, position, tilt angle and shape. The system may include the processor which may be configured to analyze a plurality of historical settings, determine a trend of the historical settings, and develop an optimal setting for fitting the patient interface to the patient. The setting to be applied to the patient interface may be an average of the at least one historical setting.

Some versions of the technology may include a patient interface for sealed delivery of a flow of breathable gas to a patient's airway, which may include a sealing structure to form a seal on the patient's face and a plurality of capacitive sensors coupled to the sealing structure, each sensor disposed at a different location on the sealing structure, each sensor configured to detect proximity between the sealing structure and the patient's face, each sensor adapted to couple with a processor to determine a sealing condition between the sealing structure and the patient's face based on a signal strength detected by each sensor.

In some cases, the patient interface may include the processor being configured to identify a sealing condition at each sensor location on the sealing structure. The processor may determine the sealing condition by comparing the signal strength to a predetermined threshold. The processor may determine that a touch has occurred or an excessive force has been applied against the patient's face, when the signal strength exceeds the predetermined threshold. The processor may determine no touch or an inferior touch may have occurred, when the signal strength does not exceed the predetermined threshold.

In some cases, the patient interface may include at least one of the capacitive sensors which may include a plurality of resistors in series. At least one of the capacitive sensors may include an exposed metal contact area allowing direct contact with the patient's face. At least one of the capacitive sensors may be covered by a layer of insulation. At least one of the capacitive sensors may include a copper tape. At least one of the capacitive sensors may have an oblong configuration. At least one of the capacitive sensors may be weaved into the sealing structure by at least one conductive thread.

Some versions of the technology may include a patient interface for sealed delivery of a flow of breathable gas to a patient's airway, which may include a sealing structure to form a seal on the patient's face and a capacitive sensor including a copper tape coupled to the sealing structure, the sensor adapted to couple with a processor to determine proximity between the sealing structure and the patient's face. The copper tape may have an oblong shape. The copper tape may have dimensions of approximately 15 mm by 10 mm by 0.06 mm. The copper tape may be attached to an inner membrane of the sealing structure. The copper tape may be attached to an outer membrane of the sealing structure.

Some versions of the technology may include a patient interface for sealed delivery of a flow of breathable gas to a patient's airway, which may include a sealing structure to form a seal on the patient's face and a capacitive sensor including textile coupled to the sealing structure, the sensor adapted to couple with a processor to determine proximity between the sealing structure and the patient's face. The capacitive sensor may be weaved into the sealing structure by a conductive thread. The capacitive sensor may include a conductive path to transmit information to the processor.

Some versions of the technology may include a patient interface for sealed delivery of a flow of breathable gas to a patient's airway, which may include a sealing structure to form a seal on the patient's face and a resistive sensor coupled to the sealing structure, the resistor sensor including a pair of parallel conductive elements placed on the sealing structure, the sensor adapted to couple with a processor to determine proximity between the sealing structure and the patient's face. The resistive sensor may be exposed on an outer membrane of the sealing structure. The resistive sensor may include material coated in conductive paint. The resistive sensor may include a pair of parallel touch pads.

In some versions, each touch pad of the patient interface may include a conductive path. The pair of parallel touch pads may be arranged in an interlaced or cross-linked fashion. The patient interface may include resistive sensor which may have a tin-coated copper wire arranged in an interlaced fashion. The resistive sensor may have a conductive yarn arranged in an interlaced fashion. The patient interface may include the processor which may determine proximity between the patient interface and the patient by comparing a signal generated by the resistive sensor to a predetermined threshold.

Some versions of the technology may include a patient interface for sealed delivery of a flow of breathable gas to a patient's airway, which may include a sealing structure to form a seal on the patient's face and a resistive ink bend sensor coupled to the sealing structure, the sensor adapted to couple with a processor to determine proximity between the sealing structure and the patient's face. The resistive ink bend sensor may include a conductive ink. The conductive ink may be transferred (e.g., printed or painted etc.) on the sealing structure. The conductive ink may be transferred (e.g., printed or painted etc.) on a plastic film. The plastic film may be assembled to the sealing structure.

In some versions, the patient interface may include the sensor which may generate a signal indicative of at least one of bonding, movement, vibration, humidity, and deflection of the patient interface. The sensor may be a unipolar sensing device. The sensor may include an ink transferred (e.g., printed or painted etc.) on one side of the sealing structure. The sensor may produce an increasing resistance signal as the sensor deflects in one direction. The sensor may be a bipolar sensing device. The sensor may include ink transferred on both inner and outer surfaces of the sealing structure. The sensor may produce a signal indicative of any one of the following: (1) the sealing structure is sealed against the patient, (2) the sealing structure is in a nominal position, (3) the sealing structure is overcompressed, (4) the sealing structure is under compressed, and (5) the sealing structure is hyper-extended, Some versions of the technology may include a patient interface for sealed delivery of a flow of breathable gas to a patient's airway, which may include a sealing structure to form a seal on the patient's face and a shear sensor coupled to the sealing structure, the sensor adapted to couple with a processor to determine proximity between the sealing structure and the patient's face. The sensor may be one of a pinch shear force sensor and a miniature integrated shear sensor. The sensor may produce a signal indicative of at least one of the following: friction, normal force, normal pressure, shear force, pinch shear force, and lateral and vertical instability.

In some cases, the patient interface may include the processor which may determine a sealing condition between the patient interface and the patient based on a shear force signal produced by the sensor. The processor may determine a lack of contact between the patient interface and the patient when the shear force is approximately zero. The patient interface may include the sensor being attached to the sealing structure by an adhesive. The sensor may be co-molded with the sealing structure.

In some versions of the technology, the patient interface may include the processor which may determine a sealing condition between the patient interface and the patient based on a normal force signal produced by the sensor. The processor may determine an unintentional leak between the patient interface and the patient's face by comparing the normal force signal to a first predetermined threshold. The first predetermined threshold may be approximately zero.

In some cases, the patient interface may include the processor which may be configured to adjust the patient interface based on the proximity between the sealing structure and the patient's face to maintain the sealing structure in sealing contact with the patient. The processor may be configured to determine stability of the patient interface based on a shear force signal. The processor may compare an absolute value of the shear force signal to a second predetermined threshold. The processor may determine the patient interface is destabilized when the absolute value of the shear force signal is greater than the second predetermined threshold. The processor may determine the patient interface is stabilized when the absolute value of the shear force signal is not greater than the second predetermined threshold. The second predetermined threshold is approximately zero.

Some versions of the technology may include a patient interface for sealed delivery of a flow of breathable gas to a patient's airway, which may include a sealing structure to form a seal on the patient's face and a piezoelectric film sensor coupled to the sealing structure, the sensor adapted to couple with a processor to determine proximity between the sealing structure and the patient's face. The sensor may produce a signal indicating at least one of a seal contact pressure, a contact force, bend, unintentional leak, and a localized interface leak flow.

In some versions, the patient interface may further include a plurality of piezoelectric film sensors with different pole directions. The sensor may detect contact force by being poled across a thickness of the sealing structure. The sensor may detect bend and unintentional leak by being poled across a length of the sealing structure. The sensor may produce a voltage signal in proportion to a degree of bending of the sensor.

Optionally, in some cases, the patient interface may include the processor which may determine that the sealing structure is in contact with the patient when the sensor produces a steady voltage signal of a high magnitude. The processor may determine that the sealing structure is not in contact with the patient's face when the sensor produces a fluctuating voltage signal of a low magnitude. The sensor may produce a voltage signal in proportion to temperature. The processor may determine that the sealing structure is in contact with the patient's face when the sensor produces a voltage signal of a high magnitude. The processor may determine that the sealing structure is in contact with the patient's face when the sensor produces a voltage signal of a low magnitude.

Some versions of the technology may include a patient interface for sealed delivery of a flow of breathable gas to a patient's airway, which may include a sealing structure to form a seal on the patient's face, a positioning structure to secure the sealing structure to the patient's face, and a sensor coupled to the positioning structure to measure tension in the positioning structure, the sensor adapted to couple with a processor to determine tension in the positioning structure.

Optionally, in some cases, the patient interface may include the processor being configured to adjust the positioning structure based on the tension in the positioning structure. The processor may be configured to adjust the positioning structure to maintain the sealing structure in sealing contact with the patient's face. The processor may be configured to adjust the positioning structure to reduce its tension when the positioning structure is too tight. The processor may be configured to adjust the positioning structure to increase its tension when the positioning structure is too loose. The positioning structure may include a headgear strap that attaches the sealing structure to the patient's face.

The positioning structure or sealing structure may include a material that is piezoresistive.

Optionally, in some versions, the patient interface may include the headgear strap which may include a piezoresistive fabric. The patient interface may include the sensor which may include two probes configured to measure an electrical resistance across a length of the strap. Each probe may include a conductive strip disposed laterally across the strap. Each conductive strip may be enclosed within a cavity in the positioning structure. Each conductive strip may be sewn into the positioning structure.

In some versions of the technology, the patient interface may include the processor being configured to adjust the length of the strap or elasticity modulus of the strap based on the tension of the strap. The patient interface may include the positioning structure which may include a nylon filament and heater filament that are configured to adjust the length or tension of the positioning structure. The positioning structure may include an electro active element responsive to electrical stimulation. The electro active element may be a piezoelectric film.

Optionally, in some versions, the patient interface may include the processor being configured to output the determined tension to an output unit. The output unit may include at least one visual indicator. The patient interface may include the processor which may provide a first visual indication when the determined tension may be at about a predetermined comfortable level. The processor may provide a second visual indication when the positioning structure is too tight. The positioning structure may be removably connected to the sealing structure.

Some versions of the technology may include a patient interface for sealed delivery of a flow of breathable gas to a patient's airway, which may include a sealing structure to form a seal on the patient's face and a positioning structure to secure the sealing structure to the patient's face, the positioning structure includes a nylon filament and heater filament to maintain the sealing structure in sealing contact with the patient's face.

In some versions, the patient interface may include the positioning structure which may have an adjustable length responsive to a change of the nylon filament and heater filament. The positioning structure may have an adjustable tension responsive to a change of the nylon filament and heater filament. The heater filament is a flexible low power heating element. At least one of the nylon filament and heater filament may be coated by an electroless plating process.

Optionally, in some cases, the patient interface may include the positioning structure which may include a headgear strap. The headgear strap may contract up to 50% of its original length when heated. The positioning structures may include a plurality of filaments joined in parallel. The positioning structures may include a plurality of filaments joined in series.

Some versions of the technology may include a patient interface for sealed delivery of a flow of breathable gas to a patient's airway, which may include a sealing structure configured to form a seal on a patient's face and a piezoelectric element coupled to the sealing structure, the element configured to vary the sealing structure to form a seal on the patient's face.

In some cases, the patient interface may include the piezoelectric element being attached to the sealing structure. The piezoelectric element may be molded to the sealing structure. The piezoelectric element may be disposed in an outer membrane of the sealing structure. The piezoelectric element may eliminate an unintentional leak between the sealing structure and the patient's face when stimulated by electricity. The piezoelectric element may be attached to an inner membrane of the sealing structure. The piezoelectric element may be disposed within the sealing structure at a position such that when de-energized, the element forms a nominal cushion shape profile. The nominal cushion shape profile may be a "C" shape profile. The element may unfurl the sealing structure to form a seal with the patient's face when energized.

Some versions of the technology may include an apparatus for sealed delivery of a flow of breathable gas to a patient's airway. The apparatus may include a sealing structure to form a seal on the patient's face. The apparatus may include a sensor coupled to the sealing structure and configured to generate a sensor signal. The apparatus may include a positioning structure to secure the sealing structure to the patient's face. The apparatus may include a processor configured to determine a sealing condition between the sealing structure and the patient based on the sensor signal, and configured to adjust at least one of the sealing structure and the positioning structure to maintain the sealing structure in sealing contact with the patient's face. The apparatus may include a prediction system that predicts an unintentional leak between the sealing structure and the patient's face based on the sensor signal. The apparatus may include a learning system that learns how to fit the sealing structure to the patient's face to form a seal.

Some versions of the technology may include a method for fitting a patient interface to a patient's face. The method may include determining, by a processor, if a patient interface is used. The method may include predicting a leak between the patient interface and the patient's face based on a signal obtained from a sensor. The method may include adjusting the patient interface to maintain the patient interface in sealing contact with the patient's face. The method may include retrieving a historical setting of the patient interface for fitting the patient interface to the patient's face. The method may include determining a setting to be applied to the patient interface to form a seal with the patient's face. The method may include the sensor being located at the patient interface.

Some versions of the technology may include a method for fitting a patient interface to a patient's face, which may include determining, by a processor, if a patient interface may be used and detecting a leak between the patient interface and the patient's face based on a signal obtained from a sensor. The method may include adjusting the patient interface to maintain the patient interface in sealing contact with the patient's face. The method may include retrieving a historical setting of the patient interface for fitting the patient interface to the patient's face. The method may include determining a setting to be applied to the patient interface to form a seal with the patient's face. The method may include the sensor being located at the patient interface Optionally, in some versions, the method may include the historical setting being a user preferred setting. The historical setting may include a patient interface parameter associated with at least one of a strap length, elasticity modulus of a strap, force, pressure, position, tilt angle and shape.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1a shows a system including a patient 1000 wearing a patient interface 3000, in the form of a nasal pillows, receives a supply of air at positive pressure from a RPT device 4000. Air from the RPT device is humidified in a humidifier 5000, and passes along an air circuit 4170 to the patient 1000. A bed partner 1100 is also shown.

4.2 Respiratory System and Facial Anatomy

Figure 1A:
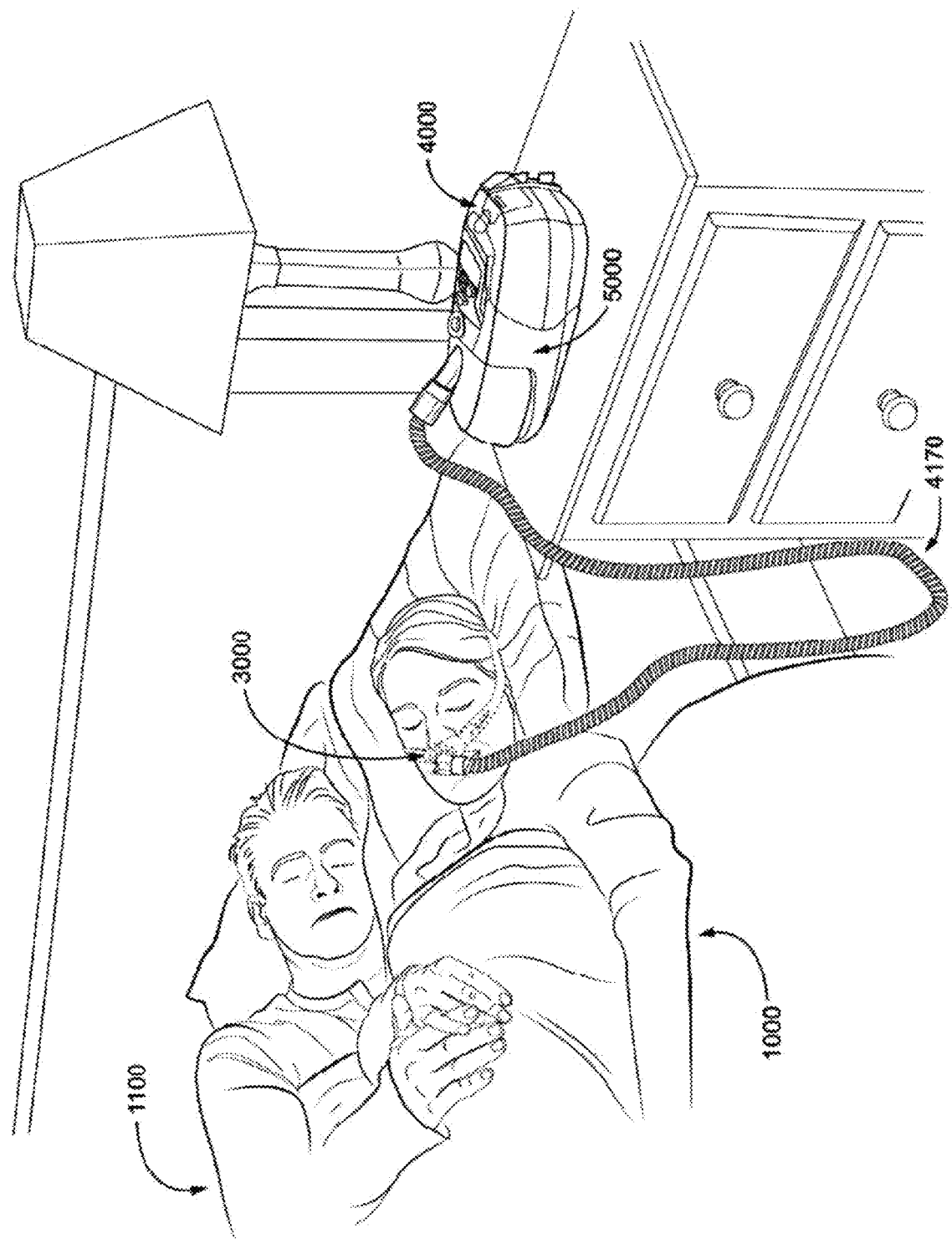
FIG. 1b shows a system including a patient 1000 wearing a patient interface 3000, in the form of a nasal mask, receives a supply of air at positive pressure from a RPT device 4000. Air from the RPT device is humidified in a humidifier 5000, and passes along an air circuit 4170 to the patient 1000.
FIG. 1c shows a system including a patient 1000 wearing a patient interface 3000, in the form of a full-face mask, receives a supply of air at positive pressure from a RPT device 4000. Air from the RPT device is humidified in a humidifier 5000, and passes along an air circuit 4170 to the patient 1000.
Figure 1C:
Figure 2A:
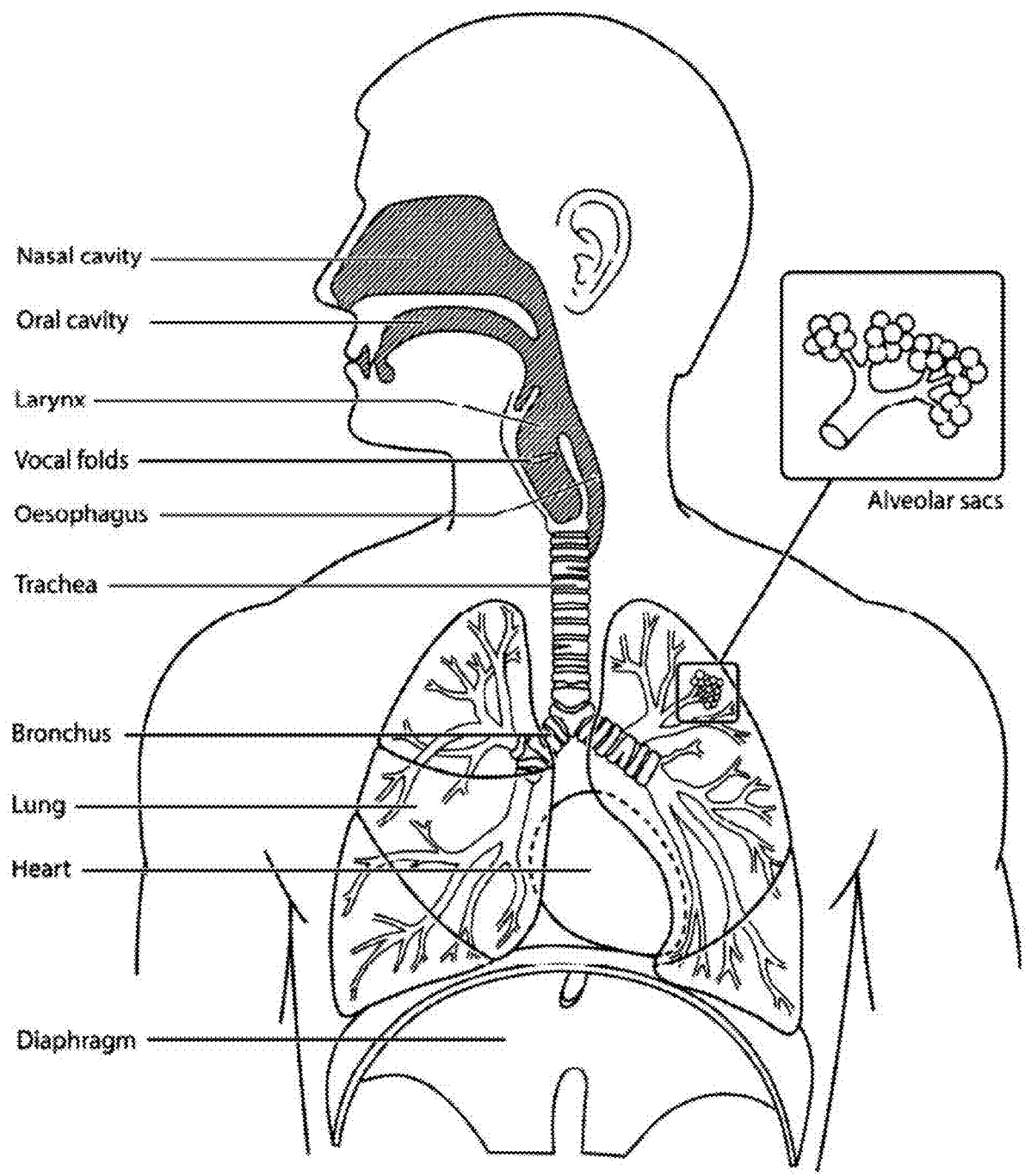

FIG. 2a shows an overview of a human respiratory system including the nasal and oral cavities, the larynx, vocal folds, oesophagus, trachea, bronchus, lung, alveolar sacs, heart and diaphragm.

Figure 2B:
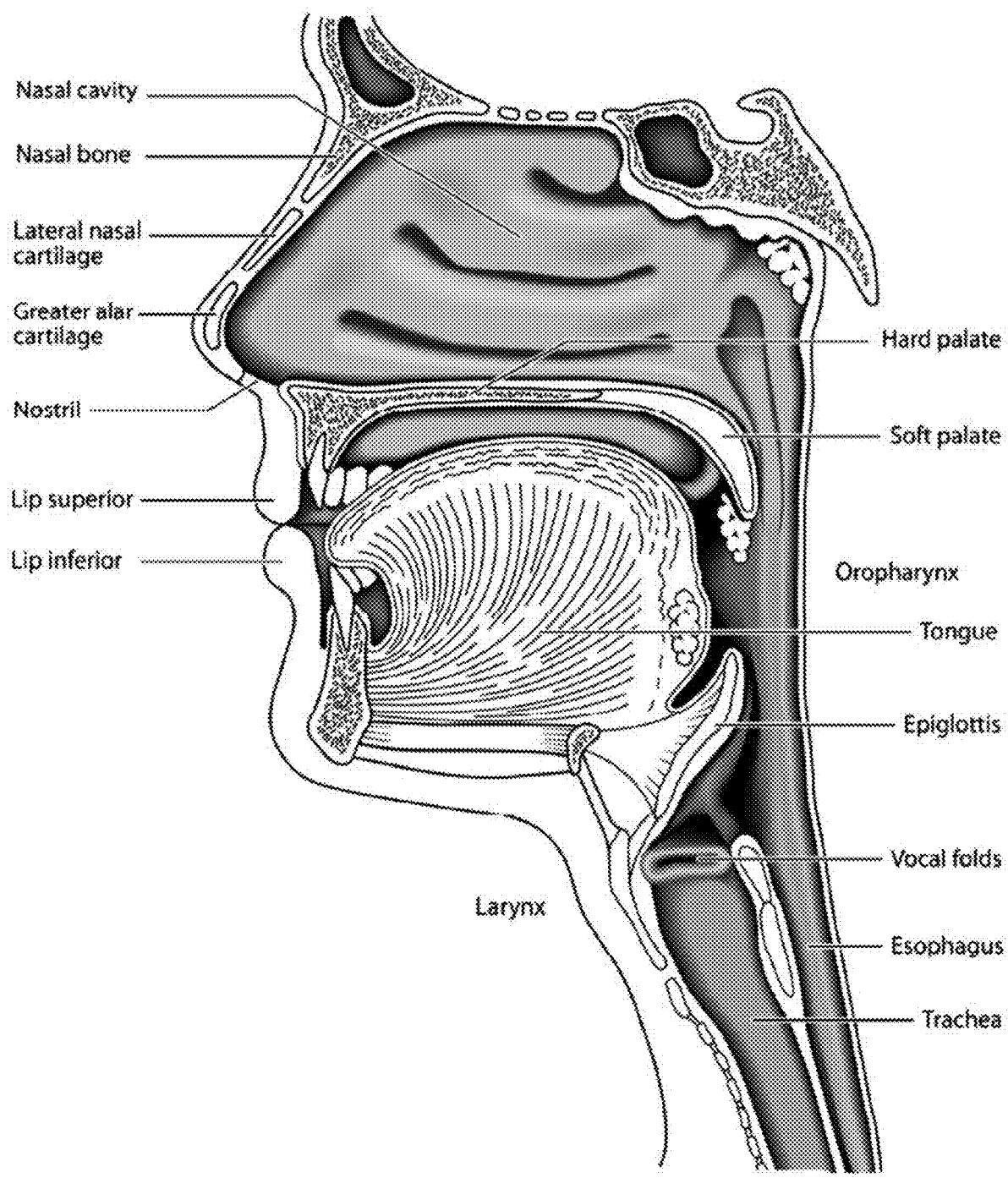

FIG. 2b shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

Figure 2C:
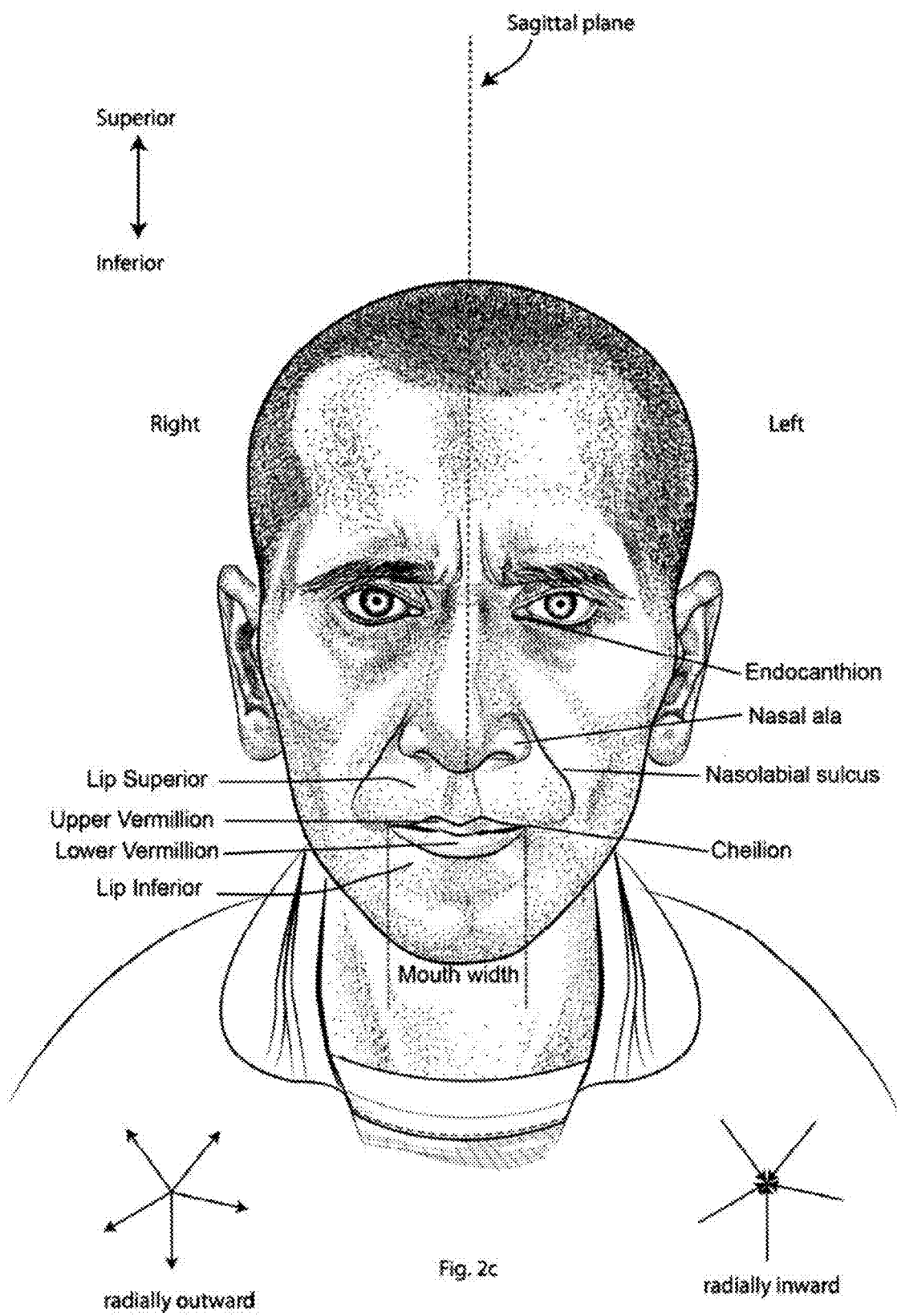

FIG. 2c is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.

4.3 Patient Interface

Figure 3A:
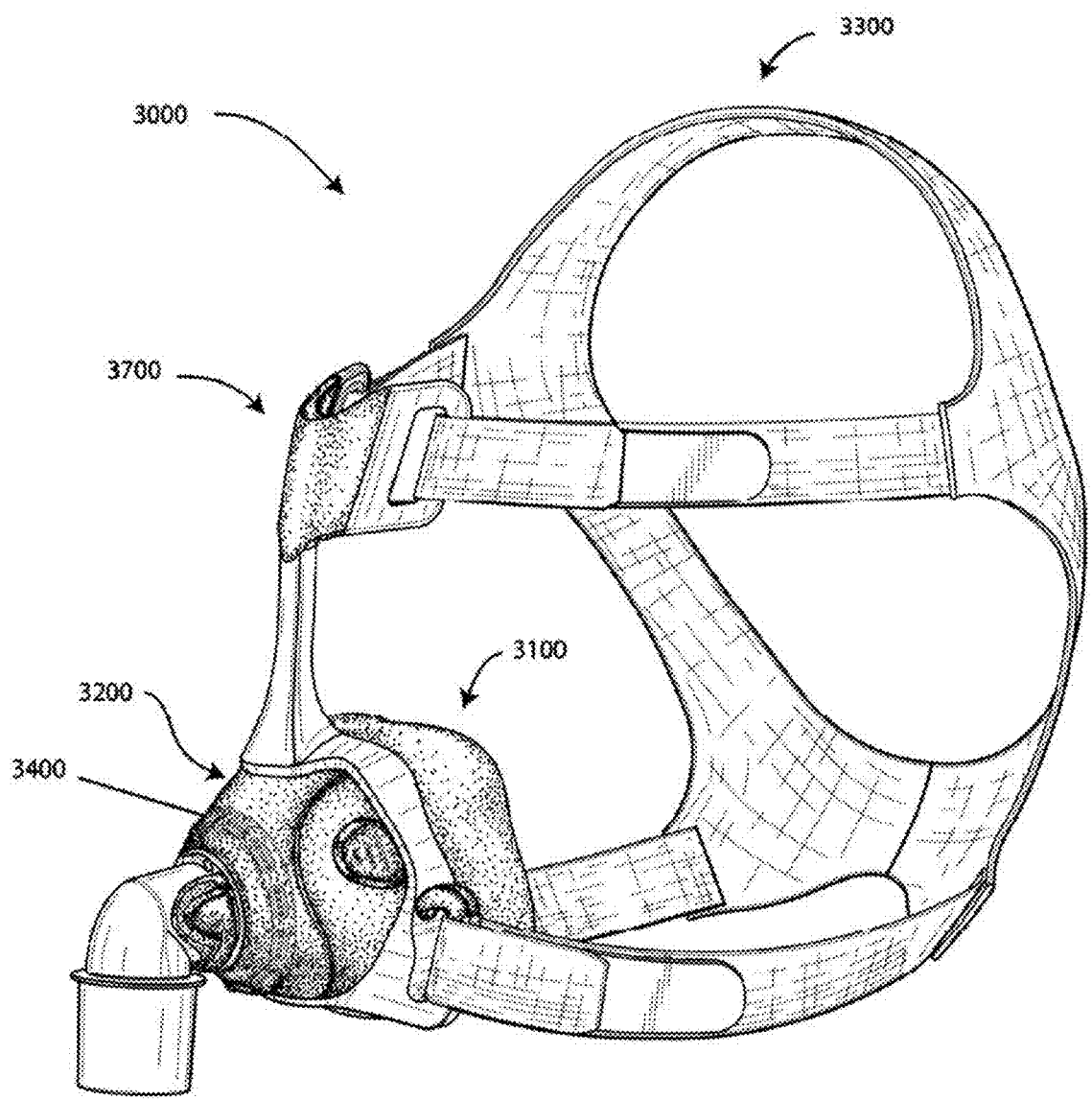

FIG. 3a shows a patient interface in the form of a nasal mask in accordance with one form of the present technology.

Figure 4A:
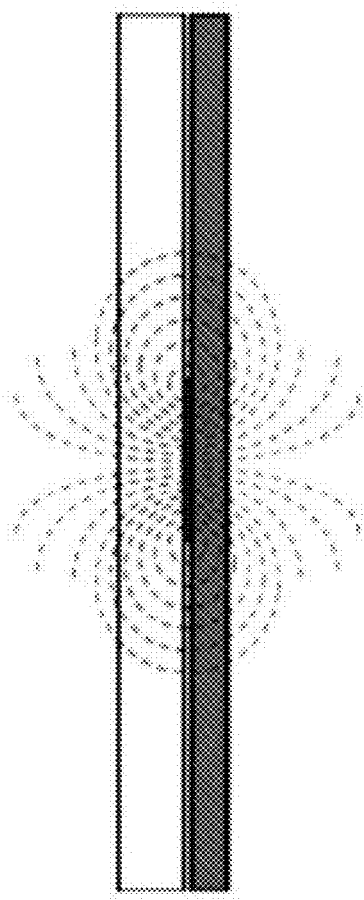

FIG. 4a shows an example of electric field lines from a capacitive sensor.

Figure 4B:
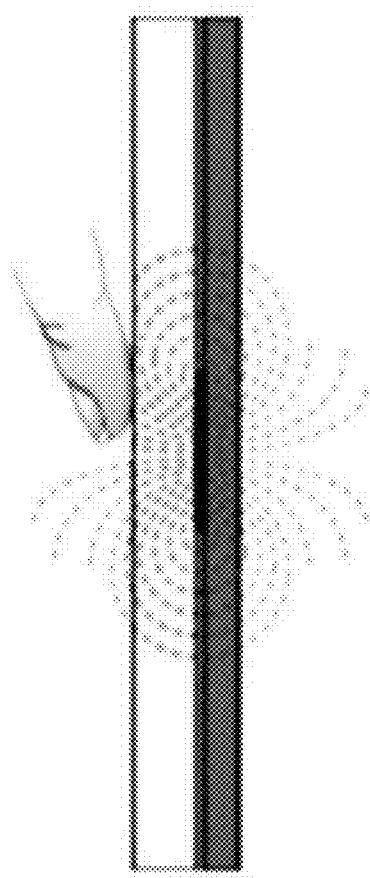

FIG. 4b shows an example of a change in the electric field lines of FIG. 4a that takes place when human interaction occurs.

Figure 5:
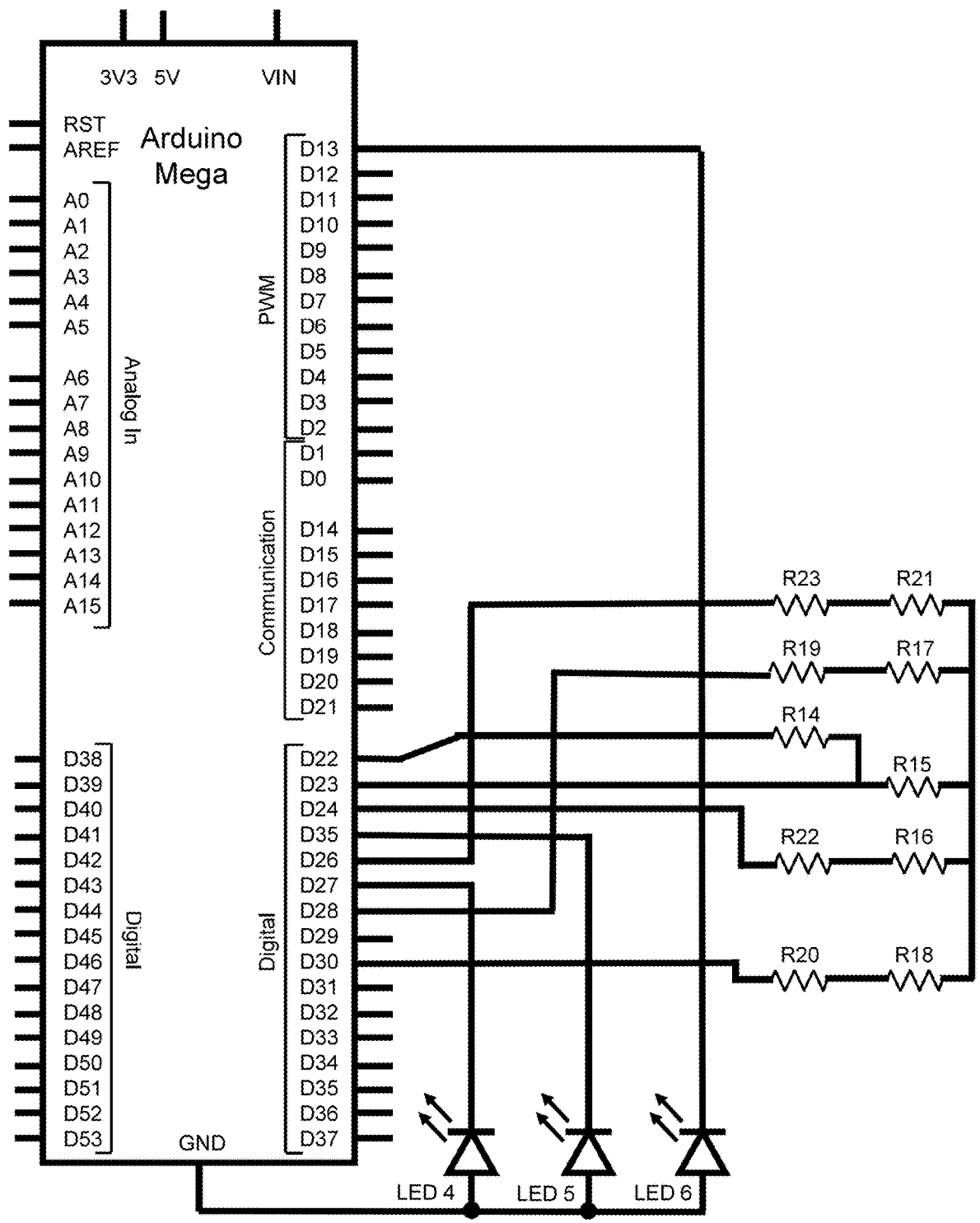

FIG. 5 shows an example schematic circuit diagram of a capacitive sensor in accordance with one form of the present technology.

FIG. 6 shows an example implementation of a patient interface with one or more copper sensors.

FIG. 7 shows an example implementation of a patient interface with one or more textile sensors.

Figure 8A:
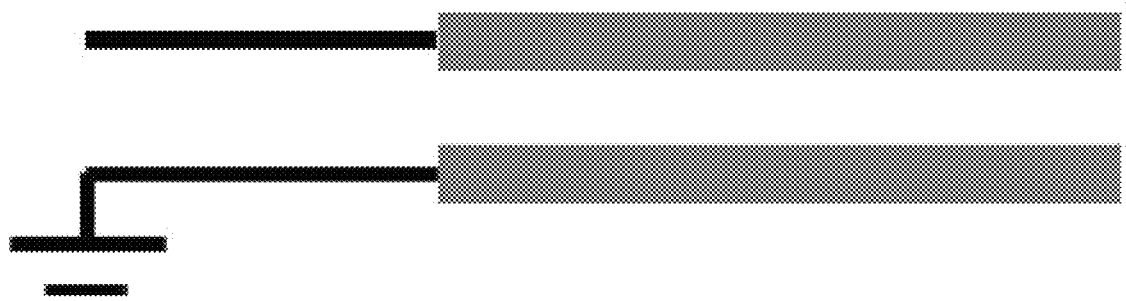

FIG. 8a shows an example of two parallel conductors without a bridge to provide a connection.

Figure 8B:
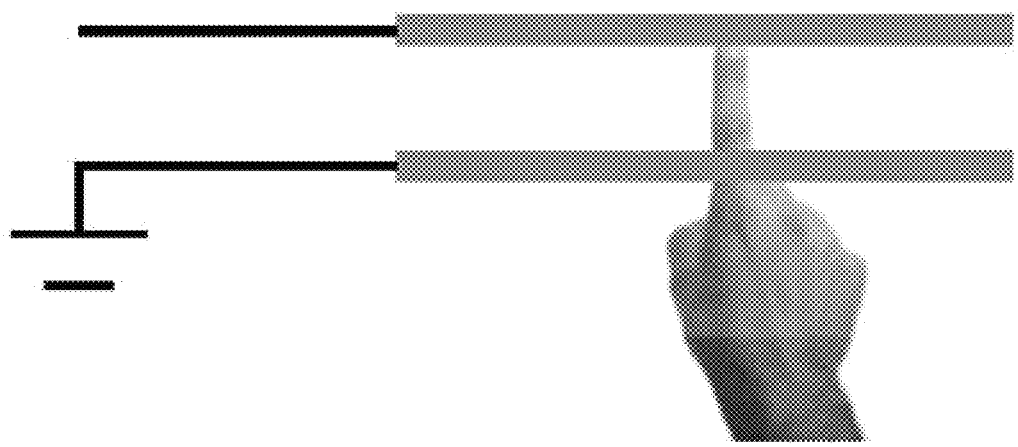

FIG. 8b shows the two parallel conductors of FIG. 8a with a human finger acting as a bridge between the two conductors.

Figure 9:
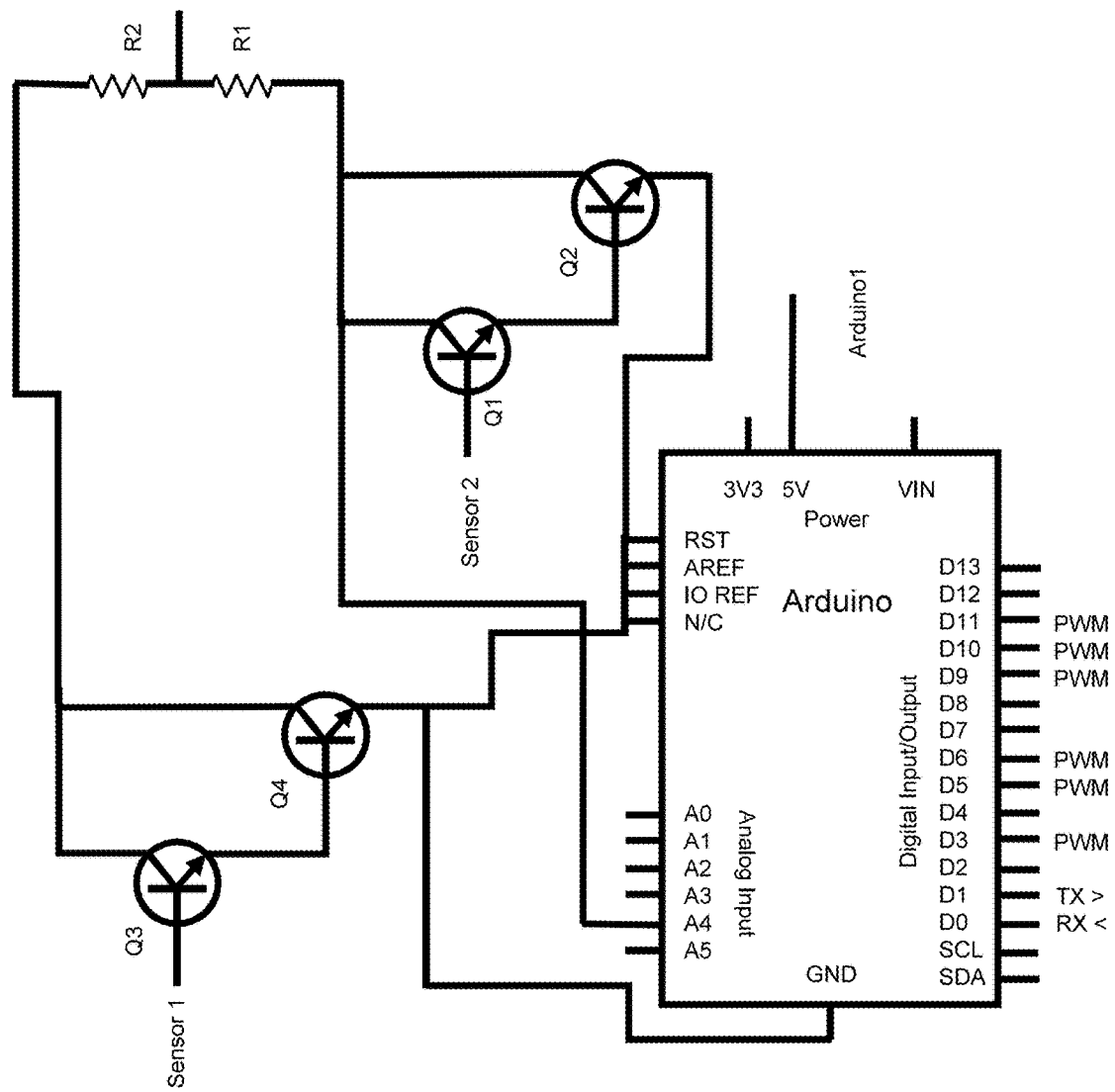

FIG. 9 shows an example schematic circuit diagram of a resistive sensor in accordance with one form of the present technology.

Figure 10:
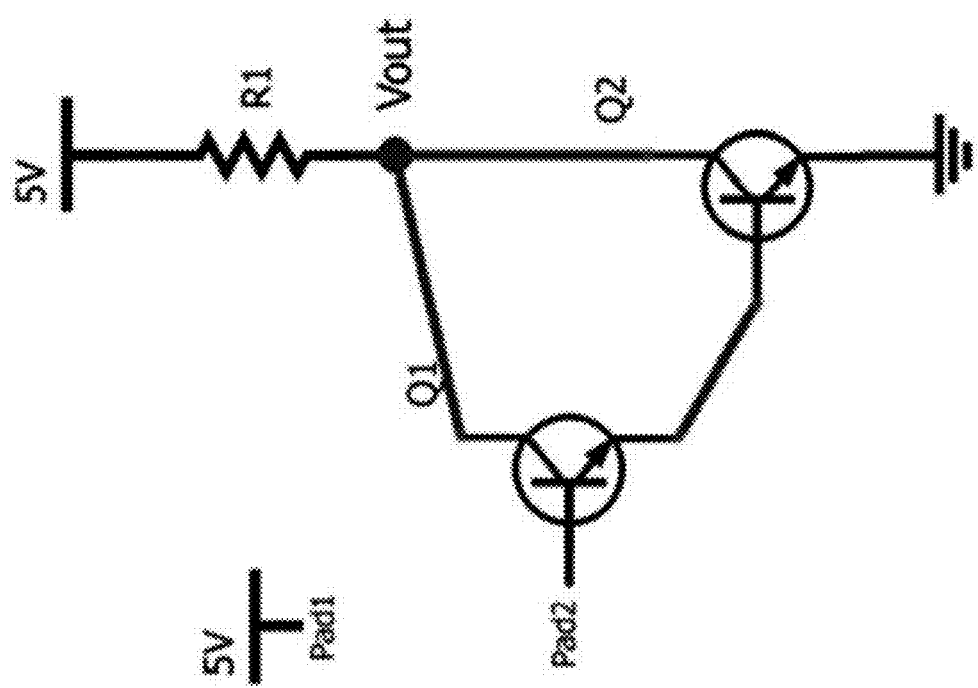

FIG. 10 shows an example schematic diagram of a resistive circuit to amplify current.

Figure 11A:
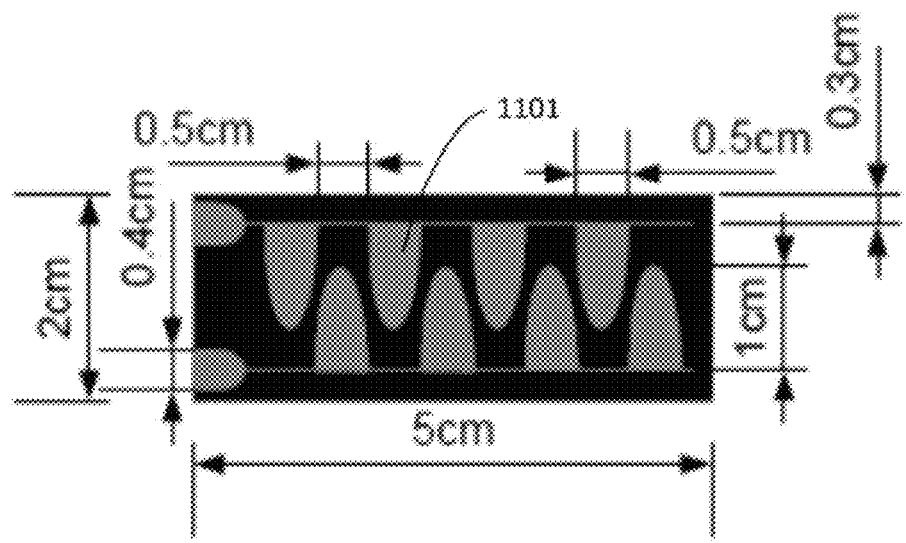

FIG. 11a shows an embodiment of a resistive sensor having conductive elements arranged in an interlaced fashion.

Figure 11B:
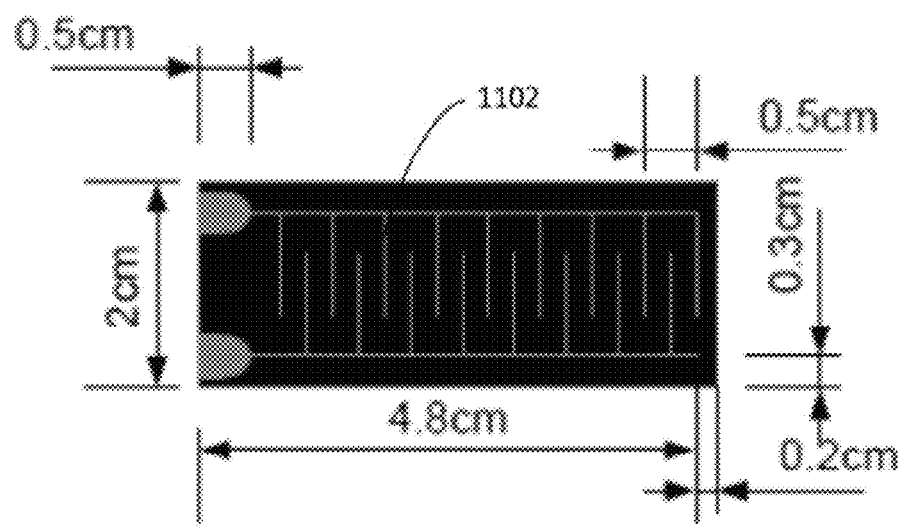

FIG. 11b shows another embodiment of a resistive sensor having conductive elements arranged in an interlaced fashion.

Figure 12:
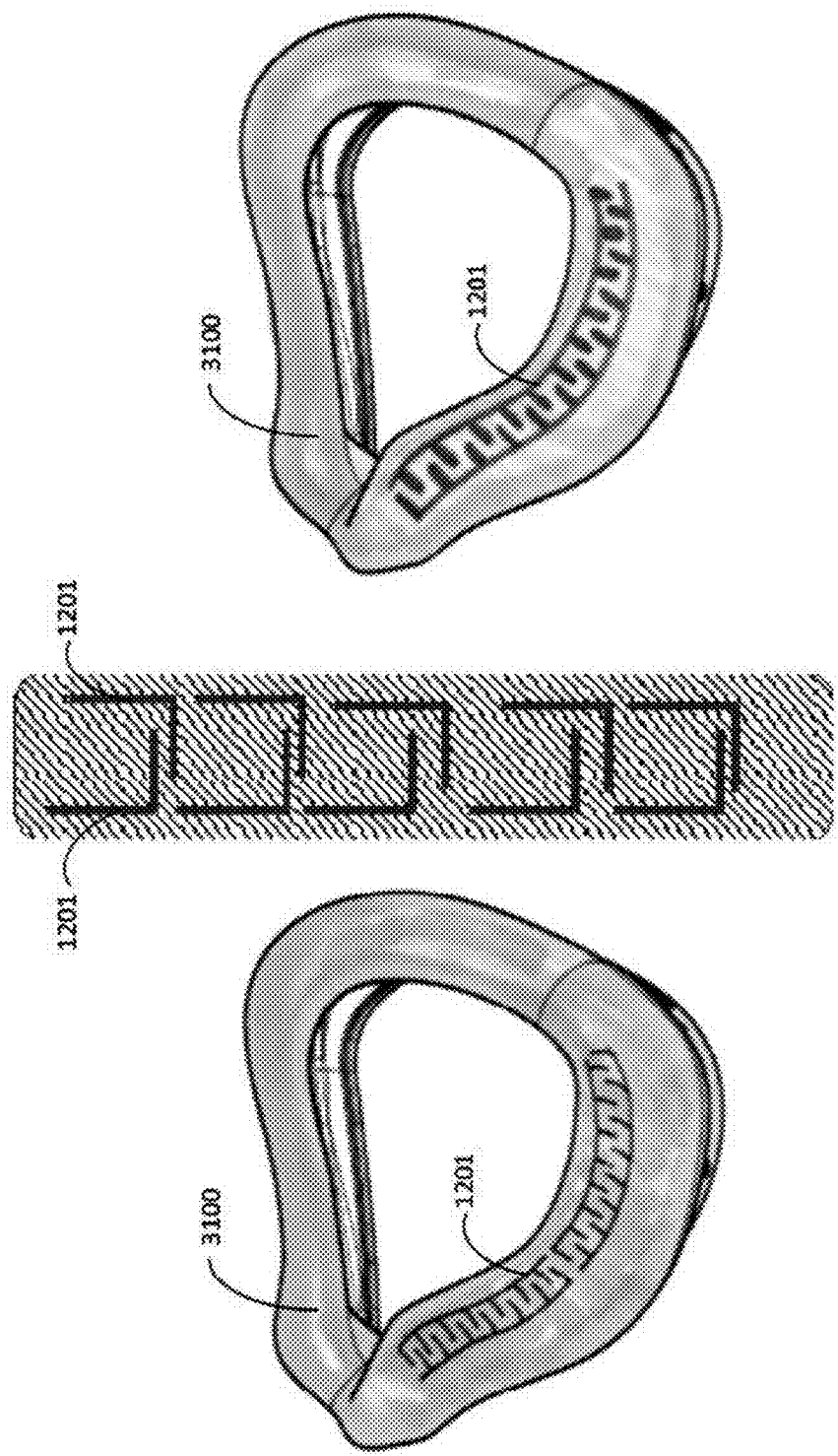

FIG. 12 shows one example of a patient interface implemented with interlaced sensors of conductive yarn or copper wire.

Figure 13:
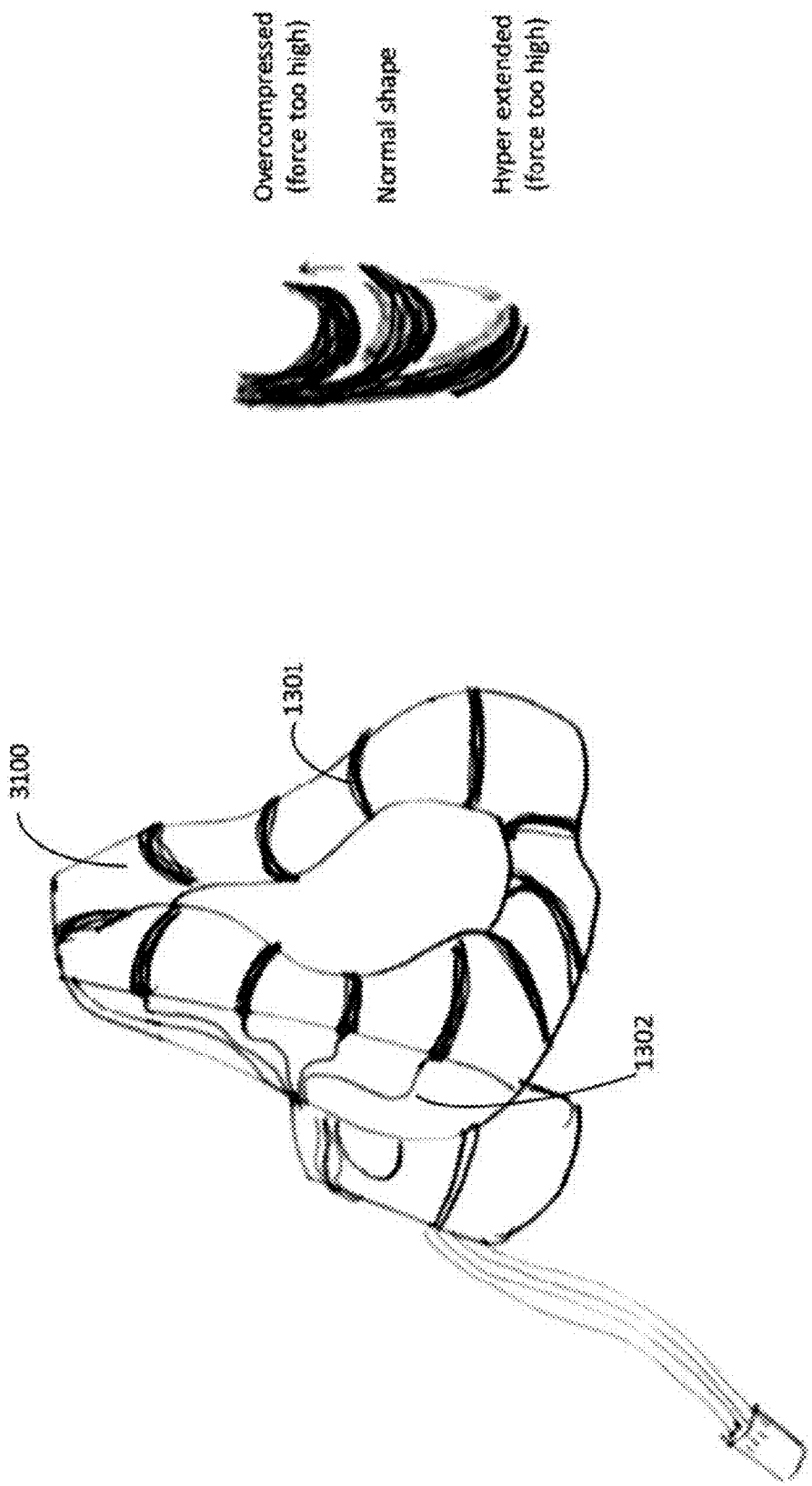

FIG. 13 shows an example patient interface implemented with resistive ink bend sensors.

Figure 14:
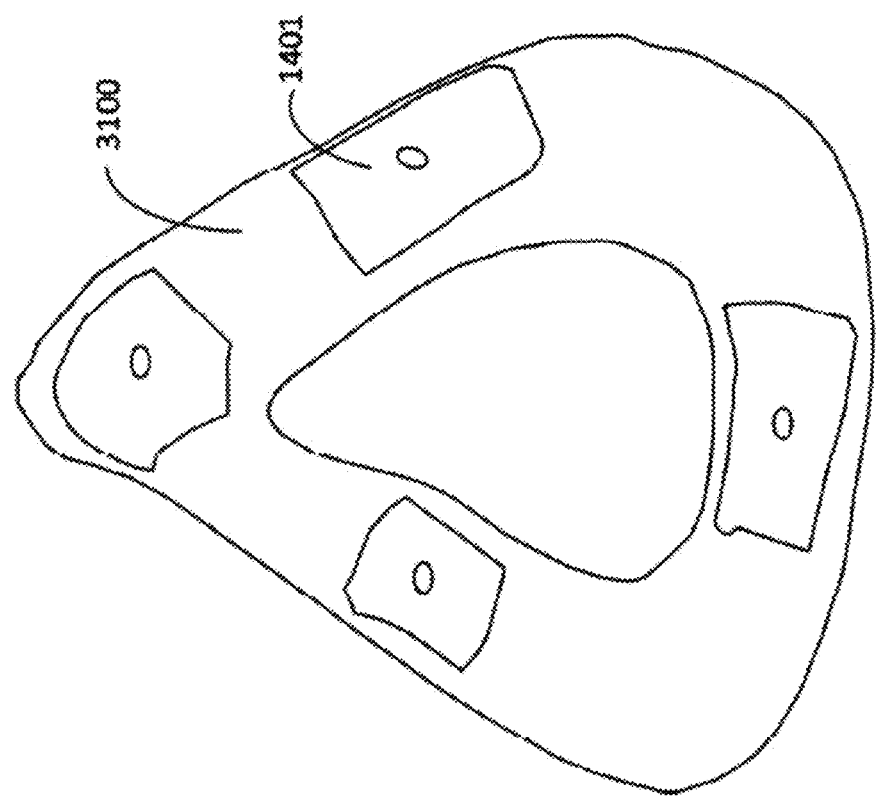

FIG. 14 shows an example patient interface implemented with shear sensors.

Figure 15:
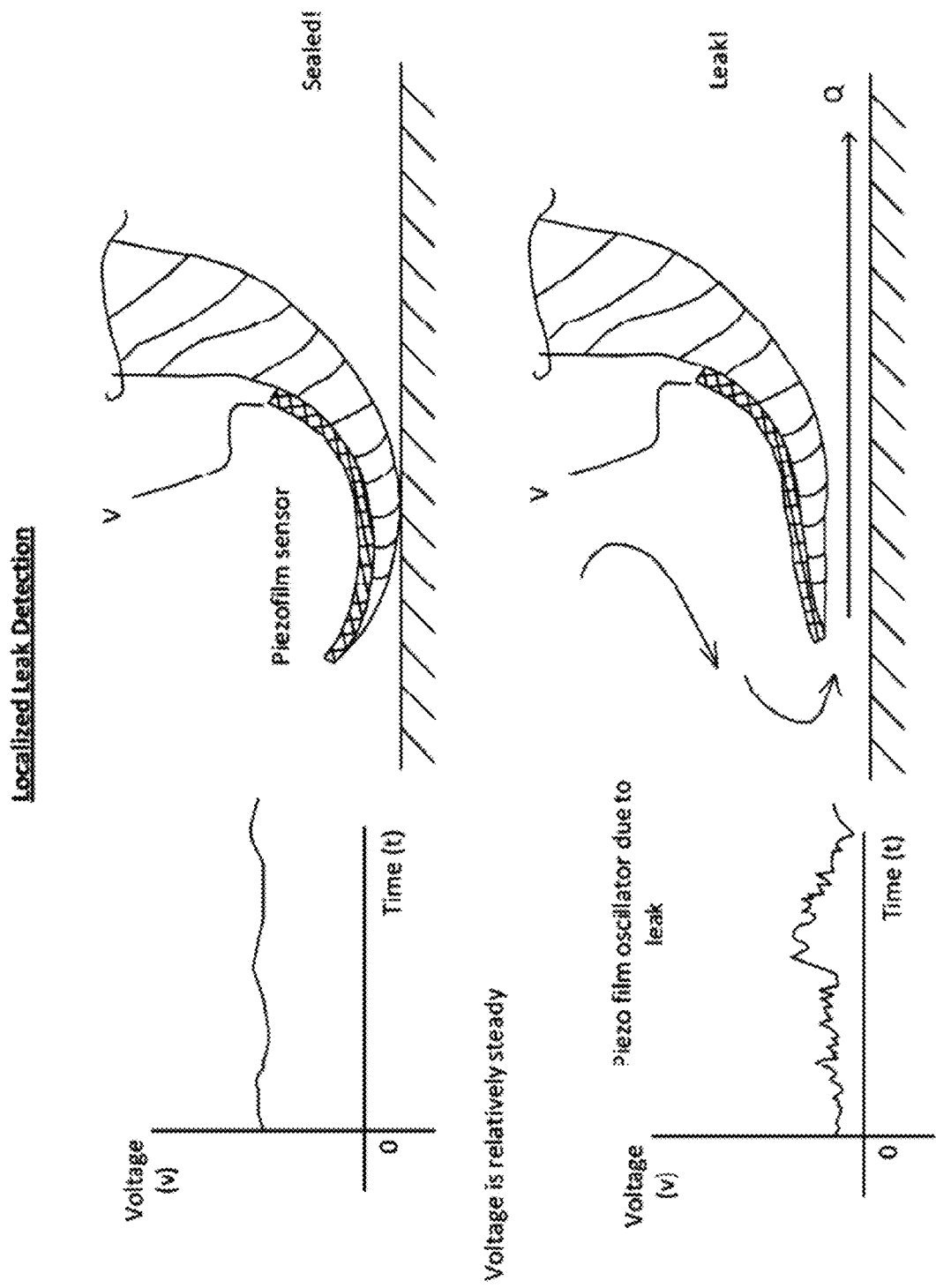

FIG. 15 illustrates a piezoelectric effect of a piezoelectric film sensor.

Figure 16:
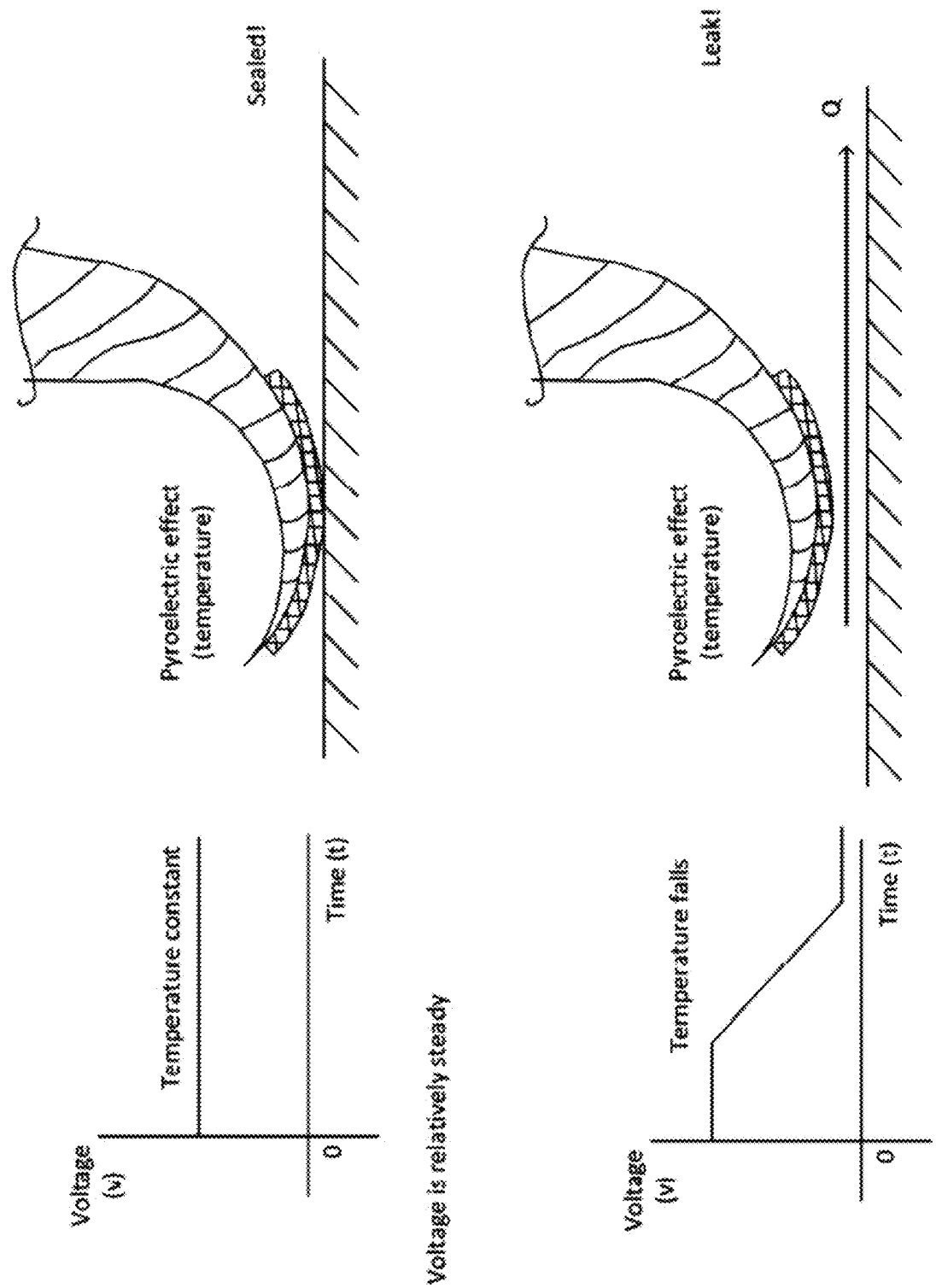

FIG. 16 illustrates a pyroelectric effect of a piezoelectric film sensor.

Figure 17:
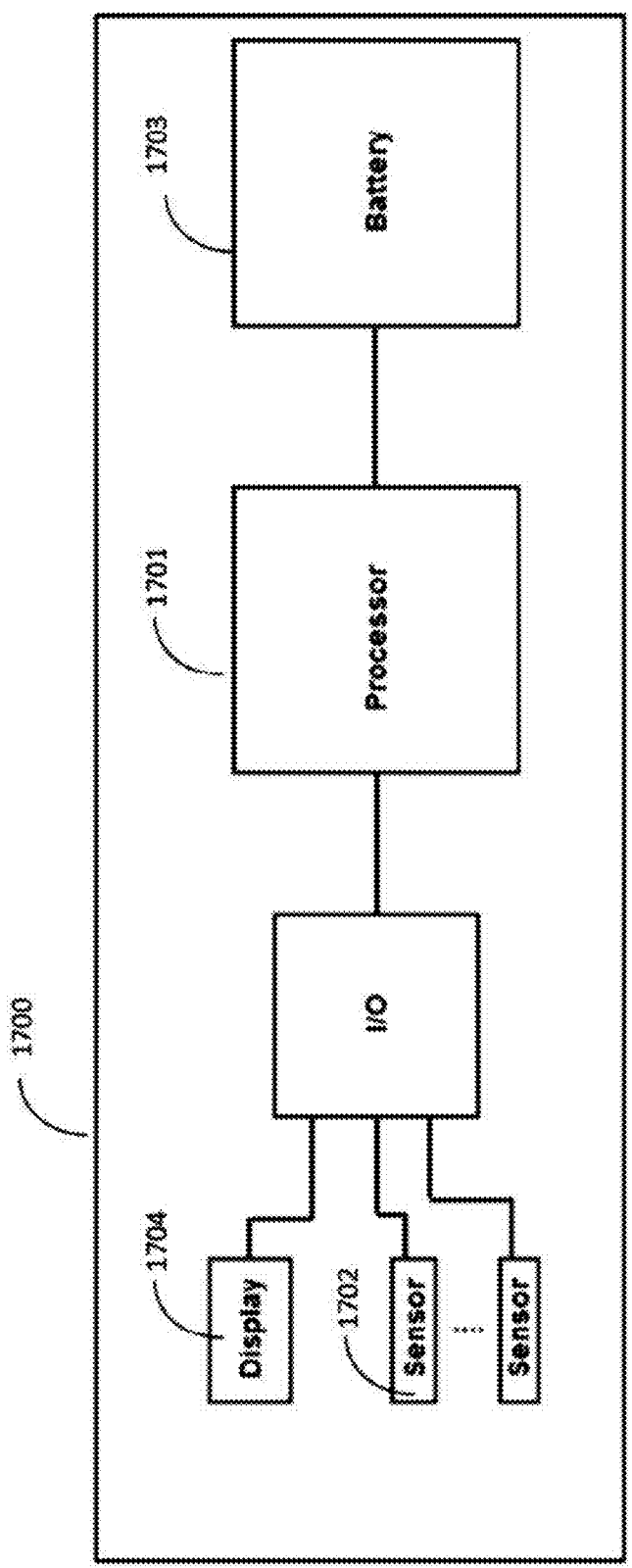

FIG. 17 shows a system architecture of an example patient interface in accordance with one form of the present technology.

Figure 18:
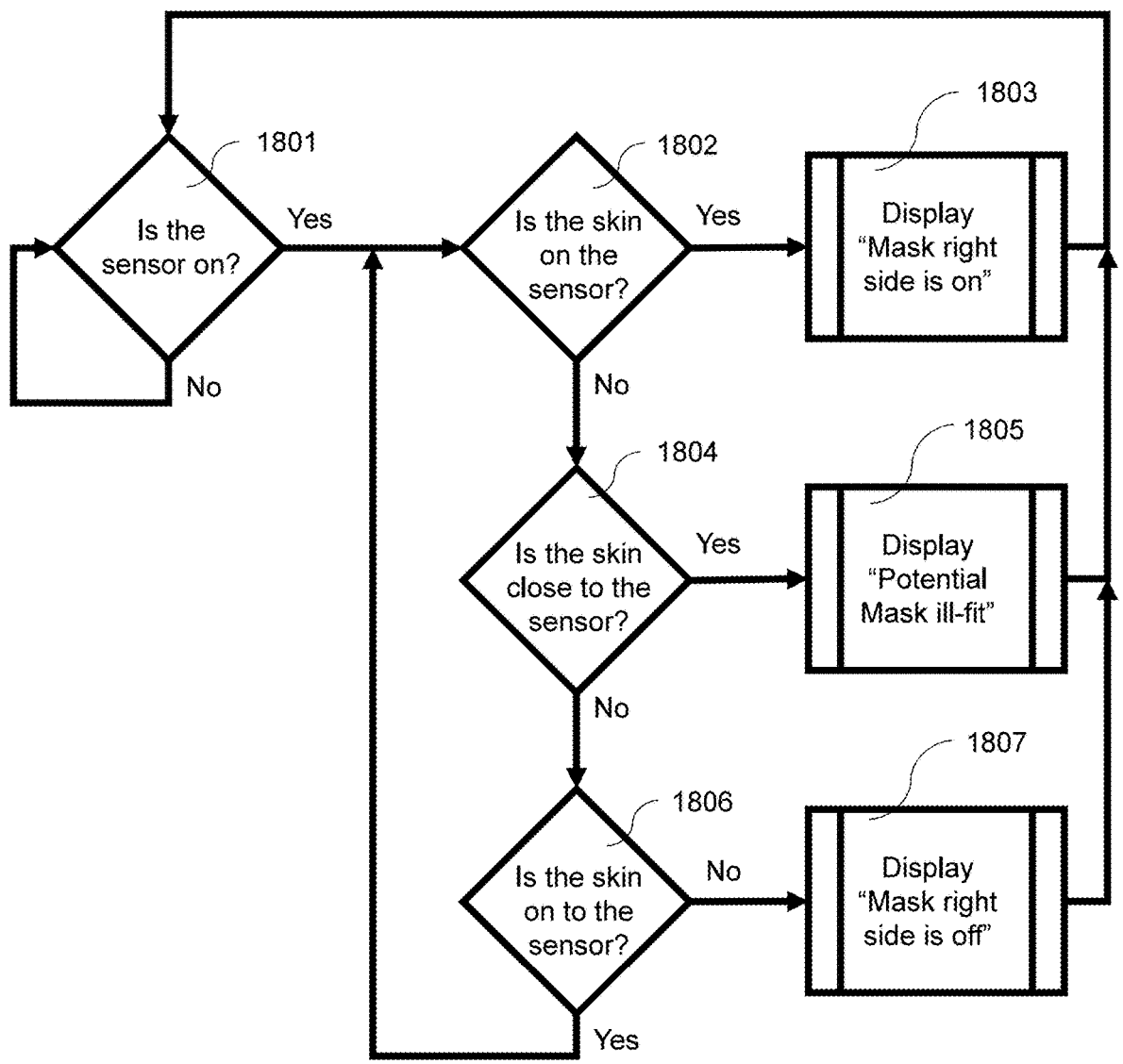

FIG. 18 illustrates a process flow diagram for processing a reading from a capacitive sensor to detect contact between a patient interface and human skin.

Figure 19:
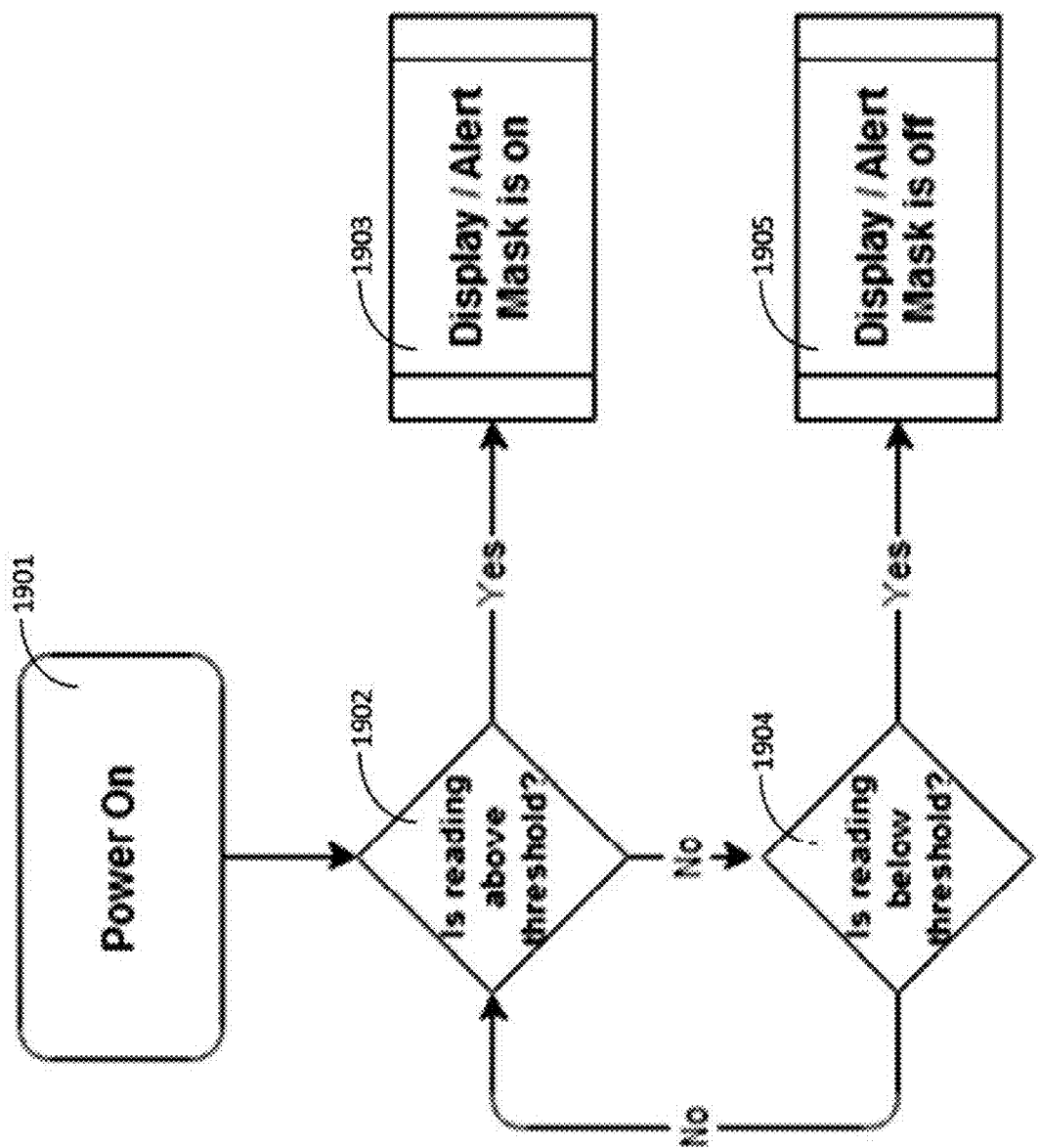

FIG. 19 illustrates a process flow diagram for processing a reading from a resistive sensor to detect contact between a patient interface and human skin.

Figure 20:
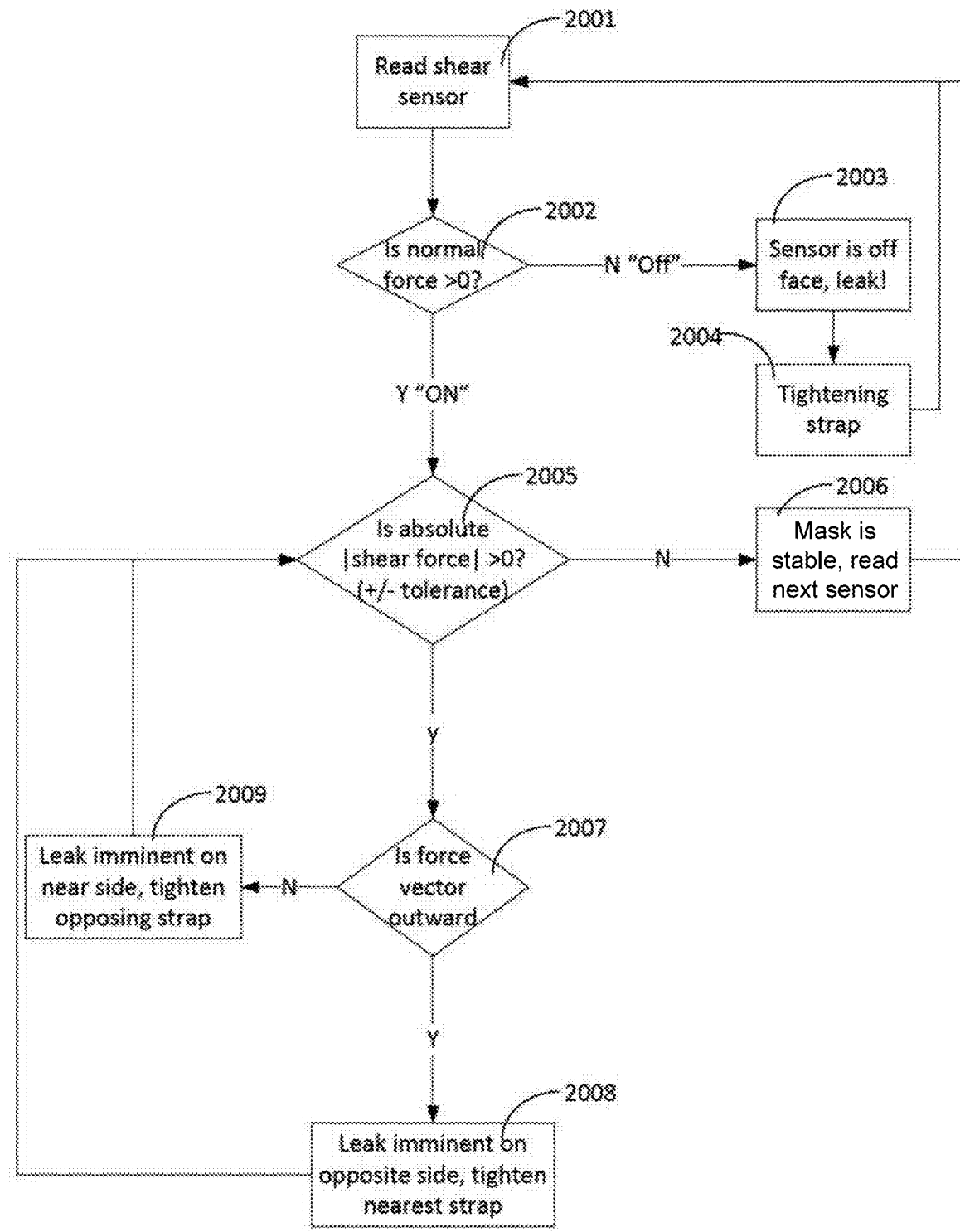

FIG. 20 illustrates a process flow diagram for processing a reading from a shear sensor to detect contact between a patient interface and human skin.

Figure 21:
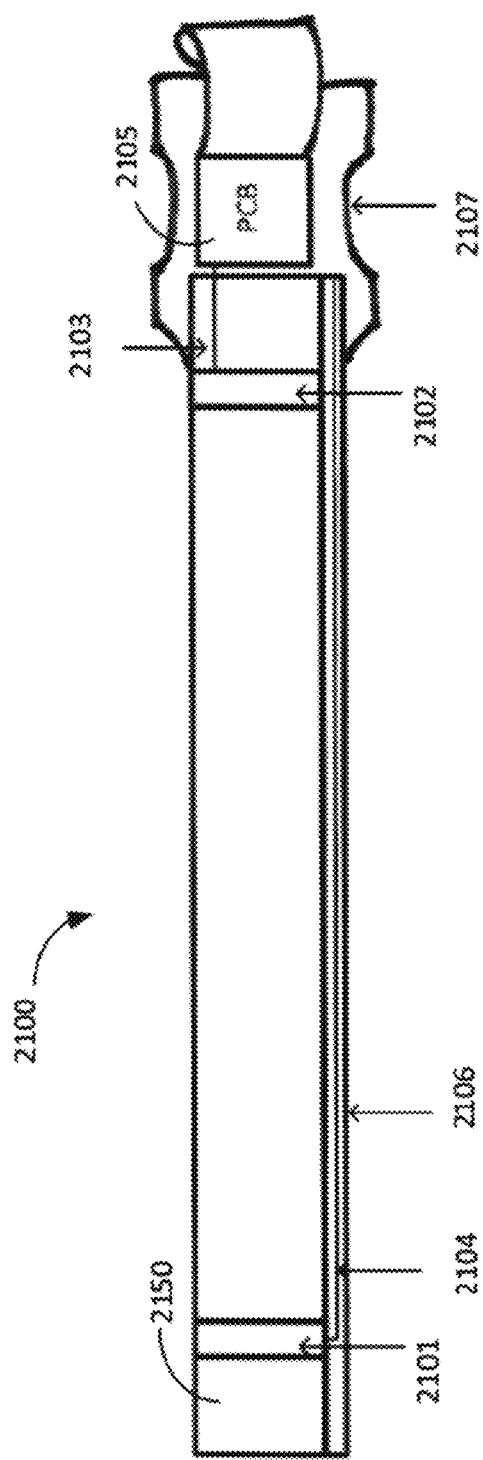

FIG. 21 illustrates an example design of a headgear strap according to one form of the present technology.

Figure 22:
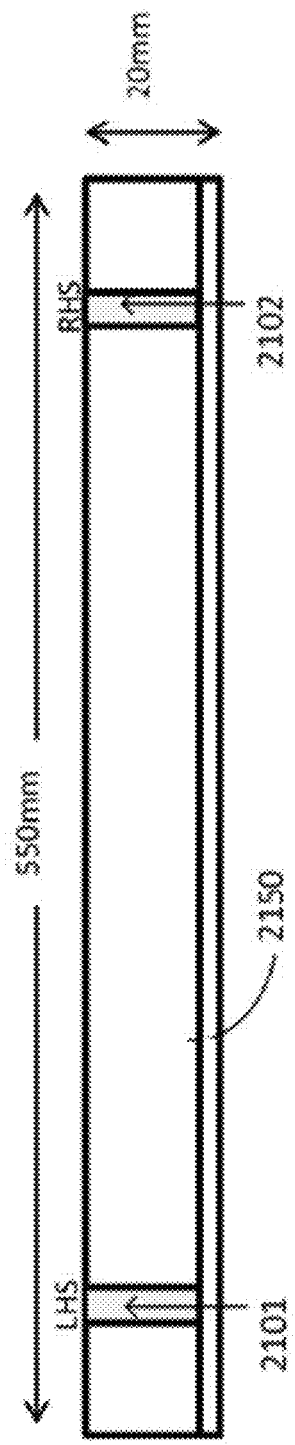

FIG. 22 illustrates an example eeonyx piezoresistive fabric implemented in the headgear strap of FIG. 21.

Figure 23:
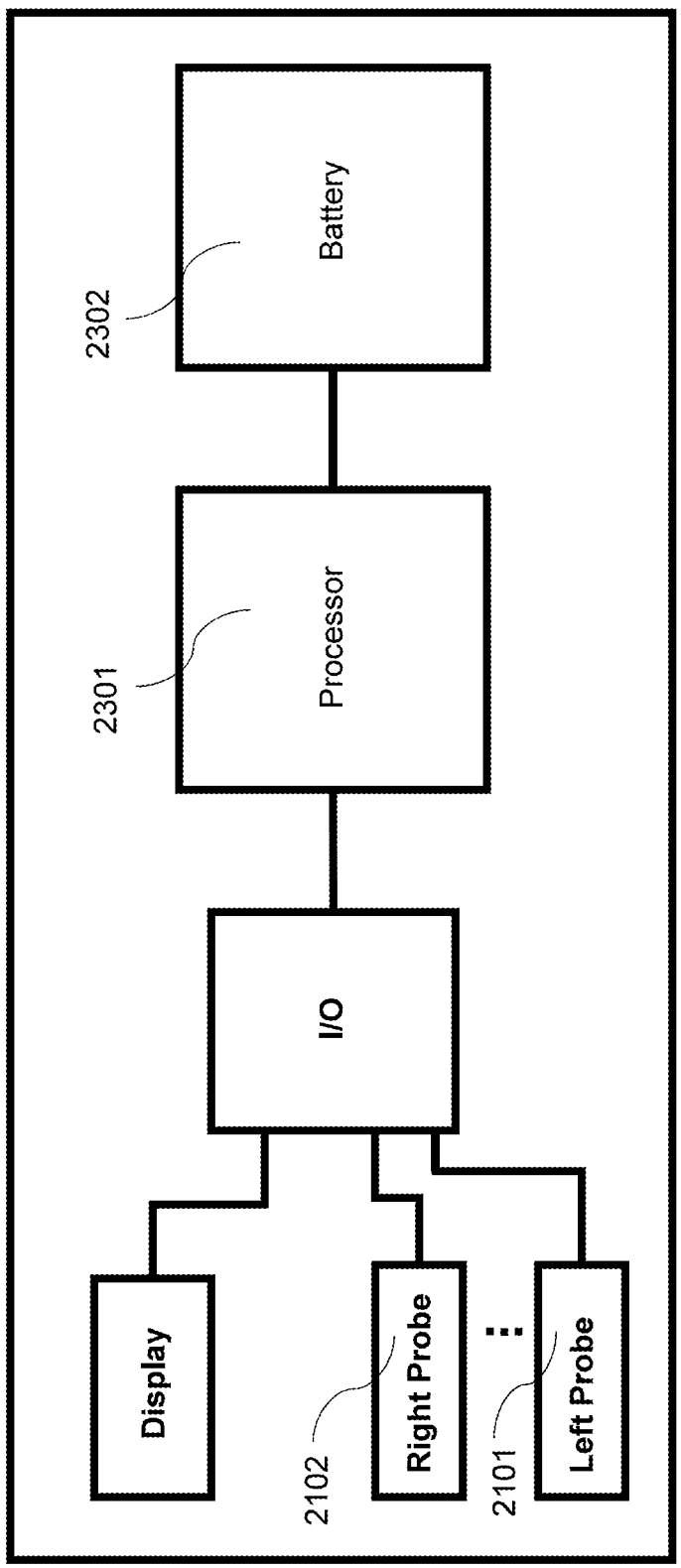

FIG. 23 illustrates an example system architecture according to one form of the present technology configured to determine tension in the headgear strap.

Figure 24:
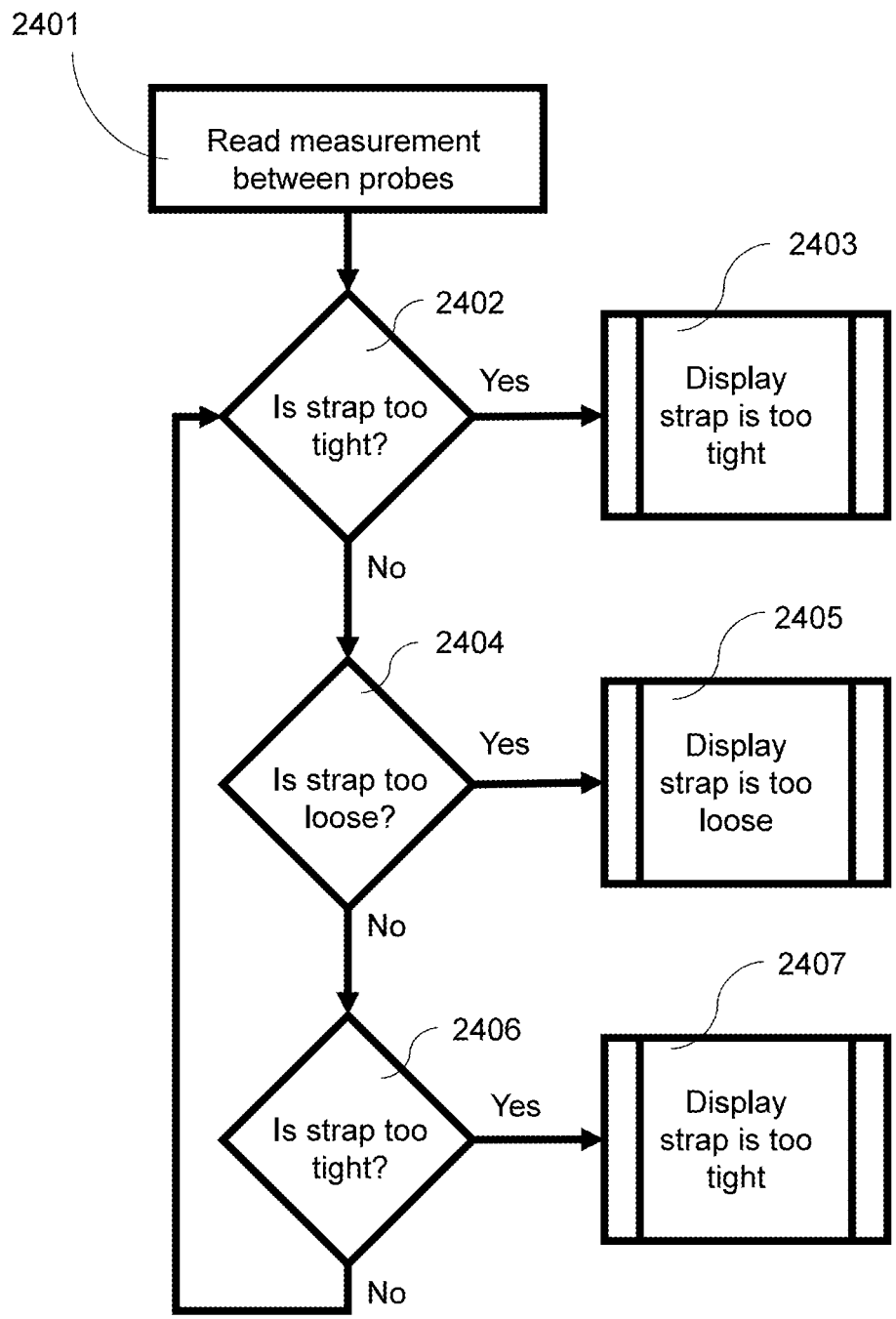

FIG. 24 illustrates a process flow diagram for detecting tension in a headgear strap.

Figure 25:
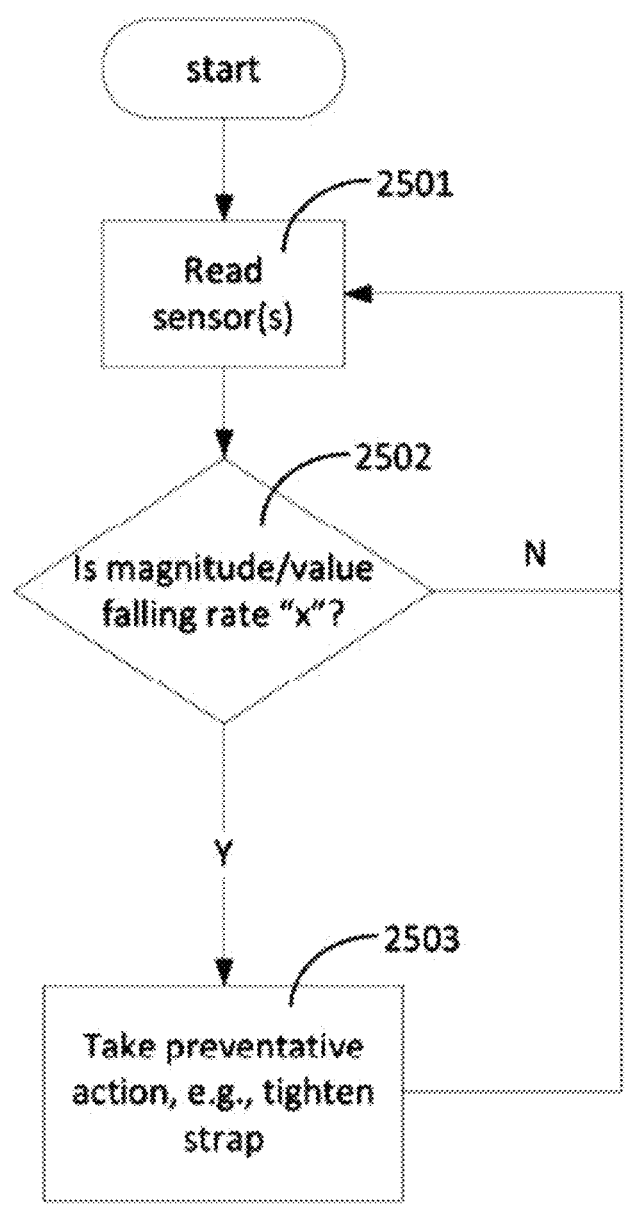

FIG. 25 illustrates a process flow diagram for predicting a leak between a patient interface and human skin.

Figure 26:
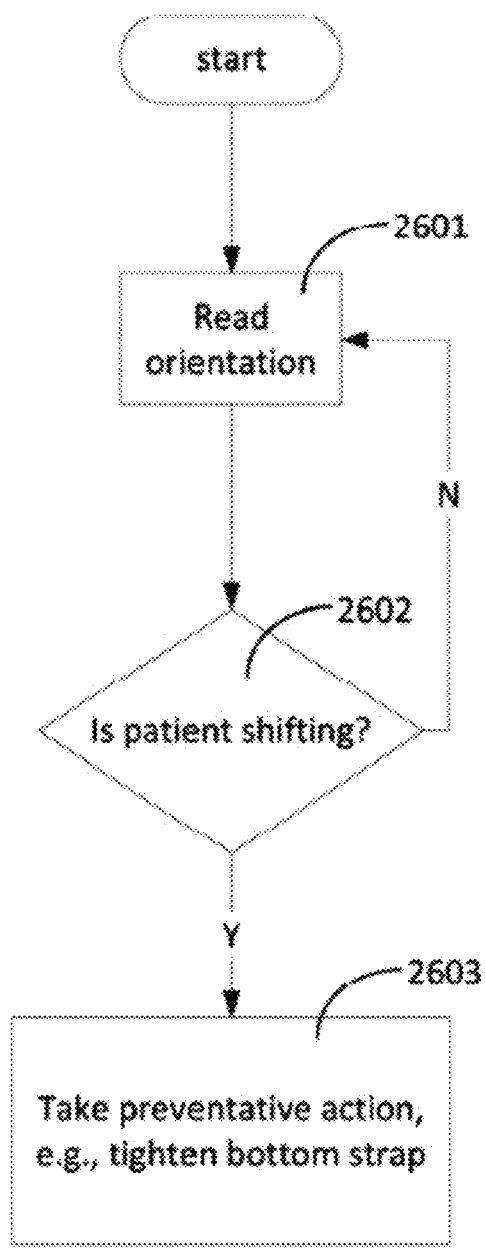

FIG. 26 illustrates another process flow diagram for predicting a leak between a patient interface and human skin.

Figure 27:
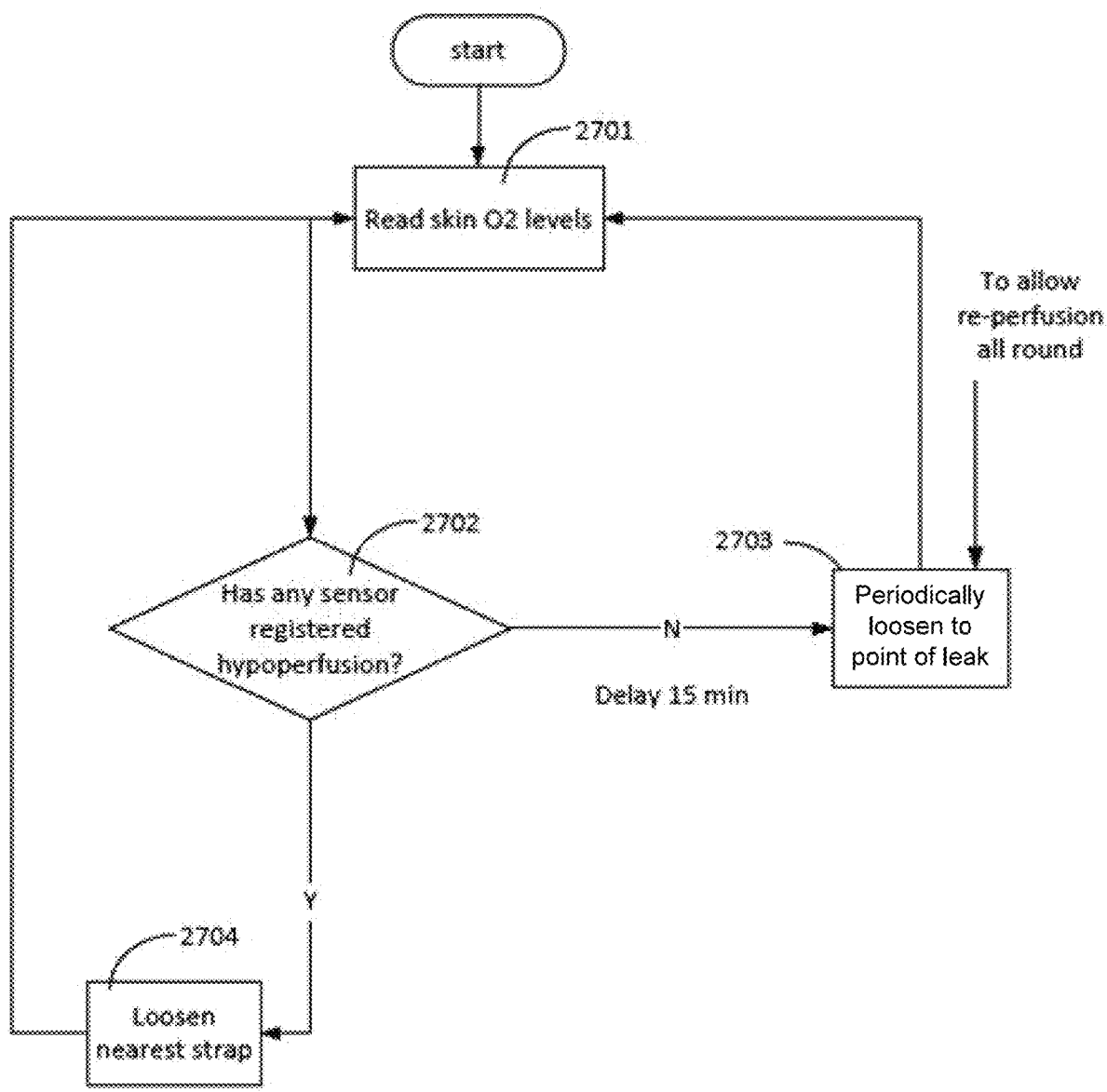

FIG. 27 illustrates yet another process flow diagram for predicting a leak between a patient interface and human skin.

Figure 28:
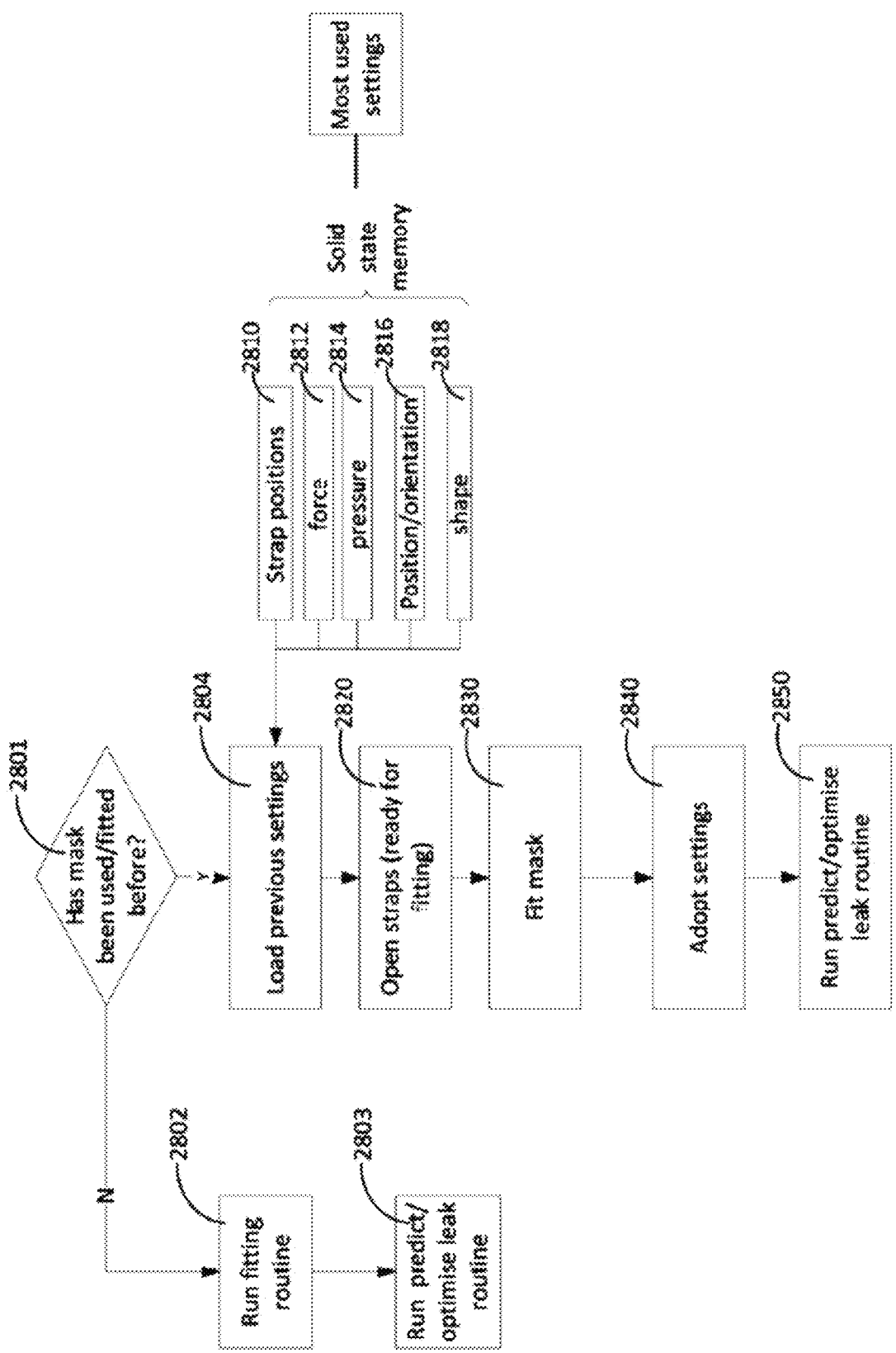

FIG. 28 illustrates a process flow diagram for fitting a patient interface to a patient.

4.4 RPT Device

Figure 29:
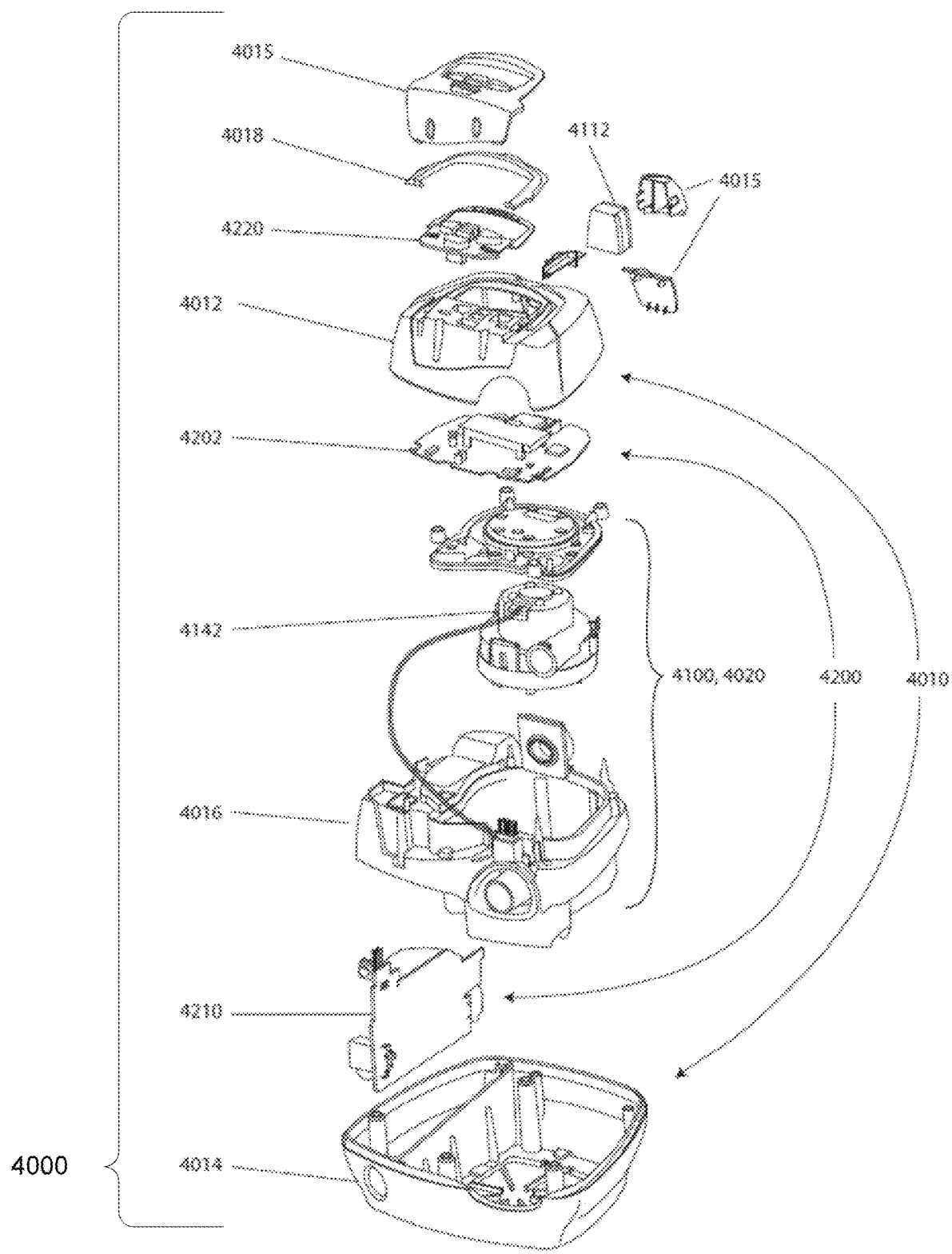

FIG. 29 shows a RPT device in accordance with one form of the present technology.

4.5 Humidifier

Figure 30:
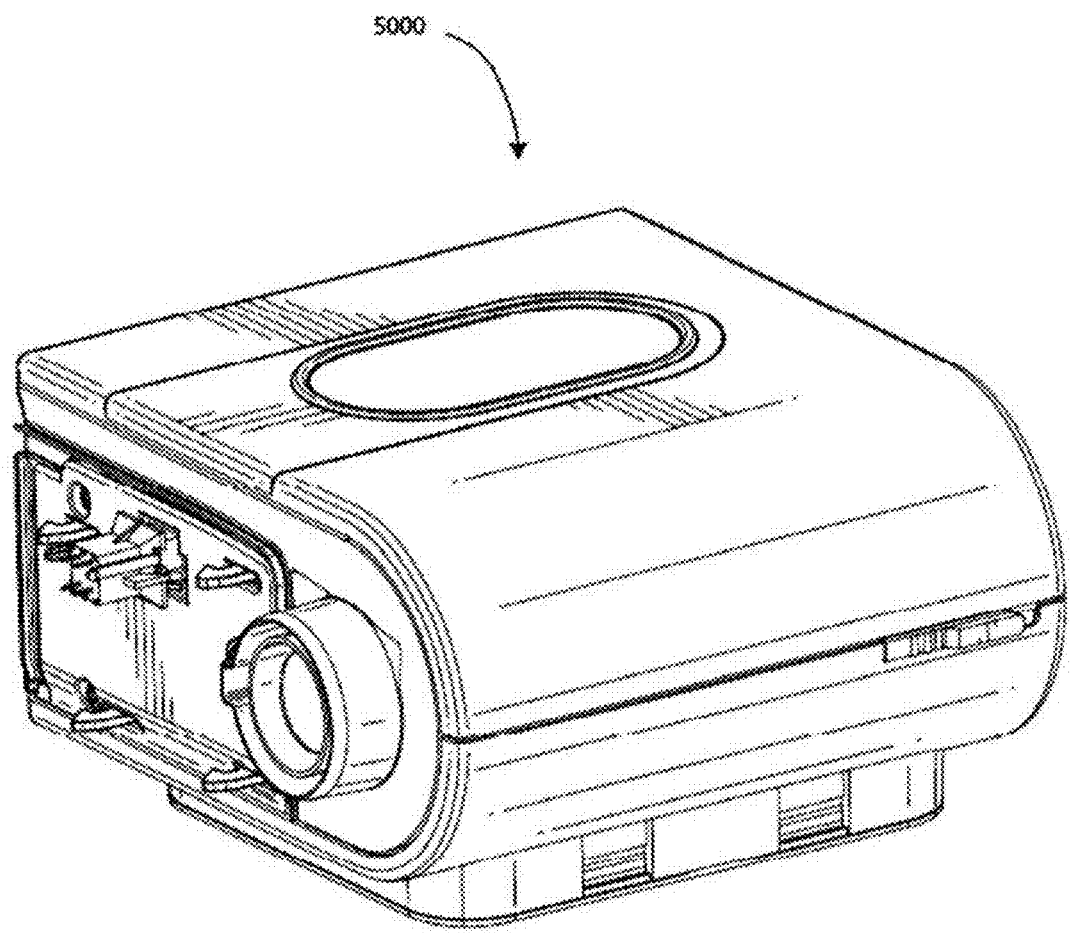

FIG. 30 shows an isometric view of a humidifier in accordance with one aspect of the present technology.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

5.1 Therapy

In one form, the present technology comprises a method for treating a respiratory disorder comprising the step of applying positive pressure to the entrance of the airways of a patient 1000.

In certain embodiments of the present technology, a supply of air at positive pressure is provided to the nasal passages of the patient via one or both nares.

In certain embodiments of the present technology, mouth breathing is limited, restricted or prevented.

5.2 Treatment Systems

In one form, the present technology comprises an apparatus or device for treating a respiratory disorder. The apparatus or device may comprise a RPT device 4000 for supplying pressurised respiratory gas, such as air, to the patient 1000 via an air circuit 4170 to a patient interface 3000.

5.3 Patient Interface 3000

A non-invasive patient interface 3000 in accordance with one aspect of the present technology comprises the following functional aspects: a seal-forming structure 3100, a plenum chamber 3200, a positioning and stabilising structure 3300 and one form of connection port 3600 for connection to air circuit 4170. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

5.3.1 Seal-Forming Structure 3100

In one form of the present technology, a seal-forming structure 3100 provides a seal-forming surface, and may additionally provide a cushioning function.

A seal-forming structure 3100 in accordance with the present technology may be constructed from a soft, flexible, resilient material such as silicone.

In one form, the seal-forming structure 3100 comprises a sealing flange 3110 and a support flange 3120. Preferably the sealing flange 3110 comprises a relatively thin member with a thickness of less than about 1 mm, for example about 0.25 mm to about 0.45 mm, that extends around the perimeter 3210 of the plenum chamber 3200. Support flange 3120 may be relatively thicker than the sealing flange 3110. The support flange 3120 is disposed between the sealing flange 3110 and the marginal edge 3220 of the plenum chamber 3200, and extends at least part of the way around the perimeter 3210. The support flange 3120 is or includes a spring-like element and functions to support the sealing flange 3110 from buckling in use. In use the sealing flange 3110 can readily respond to system pressure in the plenum chamber 3200 acting on its underside to urge it into tight sealing engagement with the face.

In one form the seal-forming portion of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose; a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement—both displacement and angular—of the frusto-cone and the structure to which the nasal pillow is connected. For example, the frusto-cone may be axially displaced towards the structure to which the stalk is connected.

In one form the non-invasive patient interface 3000 comprises a seal-forming portion that forms a seal in use on an upper lip region (that is, the lip superior) of the patient's face.

In one form the non-invasive patient interface 3000 comprises a seal-forming portion that forms a seal in use on a chin-region of the patient's face.

5.3.2 Plenum Chamber 3200

Preferably the plenum chamber 3200 has a perimeter 3210 that is shaped to be complementary to the surface contour of the face of an average person in the region where a seal will form in use. In use, a marginal edge 3220 of the plenum chamber 3200 is positioned in close proximity to an adjacent surface of the face. Actual contact with the face is provided by the seal-forming structure 3100. Preferably the seal-forming structure 3100 extends in use about the entire perimeter 3210 of the plenum chamber 3200.

5.3.3 Positioning and Stabilising Structure 3300

Preferably the seal-forming portion 3100 of the patient interface 3000 of the present technology is held in sealing position in use by the positioning and stabilising structure 3300.

5.3.4 Vent 3400

In one form, the patient interface 3000 includes a vent 3400 constructed and arranged to allow for the washout of exhaled carbon dioxide.

One form of vent 3400 in accordance with the present technology comprises a plurality of holes, for example, about 20 to about 80 holes, or about 40 to about 60 holes, or about 45 to about 55 holes.

Preferably the vent 3400 is located in the plenum chamber 3200. Alternatively, the vent 3400 is located in a decoupling structure 3500, e.g. a swivel 3510.

5.3.5 Decoupling Structure(s) 3500

In one form the patient interface 3000 includes at least one decoupling structure 3500, for example a swivel 3510 or a ball and socket 3520.

5.3.6 Connection Port 3600

Connection port 3600 allows for connection to the air circuit 4170.

5.3.7 Forehead Support 3700

In one form, the patient interface 3000 includes a forehead support 3700.

5.3.8 Anti-Asphyxia Valve 3800

In one form, the patient interface 3000 includes an anti-asphyxia valve 3800.

5.3.9 Ports 3900

In one form of the present technology, a patient interface 3000 includes one or more ports, that allow access to the volume within the plenum chamber 3200. In one form this allows a clinician to supply supplemental oxygen. In one form this allows for the direct measurement of a property of gases within the plenum chamber 3200, such as the pressure.

5.3.10 Auto-Fit Mask

According to some aspects the present technology, the patient interface 3000 may be in the form of an auto-fit mask. The auto-fit mask may have various configurations, including but not limited to, nasal masks, full-face masks, nasal pillows, nasal puffs, oro-nasal masks, and nose and mouth respiratory treatment masks.

The auto-fit mask may fit human skin, such as human face, automatically, requiring minimal or no human interaction. The auto-fit mask may have many practical benefits. For instance, when the patient is asleep, the mask may actively deal with tube torque when the patient moves during sleep. In another example, if the patient needs to go to the bathroom at night, the auto-fit mask may automatically adjust itself to seal against the patient's face once the patient returns back to bed.

To automatically adjust itself to maintain an optimal seal with human skin, the auto-fit mask may include integrated smarts. Such integrated smarts may include one or more of the following components: a sensor, a processor or information interpreter, a reactive or adjusting component, a prediction system that predicts a likelihood of leakage, and a learning system.

Specific embodiments of some of the integrated smarts components are described herein.

5.3.10.1 Sensor

The auto-fit mask may be a touch-sensitive mask. The mask may include one or more sensors located around the seal-forming structure 3100. A sensor may detect contact, a lack thereof, proximity of contact, a leak, a pressure change, and an amount of contact pressure or contact force between the mask and human skin. A leak occurs when there is a lack of adequate contact between the mask and human skin. To determine if a leak occurs or is likely to occur, sensitivity of the sensors as well as the number of sensors incorporated in the mask may be taken into consideration.

In one form, one or more sensors may sense a bulk leak, that is, a leak with respect to the mask as a whole. In one form, one or more sensors may determine leaks at specific areas on the mask. For example, the mask may include an array of sensors disposed at predetermined locations on the seal-forming structure 3100. Outputs from the array of sensors may be analysed, and the exact location of each leak may be identified.

In one form, output from one or more sensors may be recorded with a time element. Both the sensor output and its time element may be used together to predict a likelihood of a seal loss. For example, when a sensor output fluctuates, the mask may have an unstable contact with human skin at the location of the sensor. As a result, more contact pressure may be applied at the same location to stabilize the mask relative to human skin.

The present technology may employ one or more different types of sensors to detect leakage, including but not limited to any one or more of the following: a capacitive sensor, a resistive sensor, a resistive ink bend sensor, a shear sensor, and a piezoelectric film sensor. Specific embodiments of each sensor are discussed herein.

5.3.10.1.1 Capacitive Sensor

In one form, the mask may include one or more capacitive sensors to identify areas of the mask that are in touch or not in touch with human skin. A capacitive sensor may employ the concept of capacitive touch to identify whether a human being touches the capacitive sensor. The capacitive sensor may detect contact between human skin and a sensor pad based on an interaction between human skin and an electric field of the capacitive sensor. For instance, as illustrated in FIG. 4A, in the absence of a human touch, a capacitive sensor may produce a uniform electrostatic field once a voltage is applied thereto. However, when a part of a human body, such as skin or finger, interacts with this electric field, that part of the human body may create a capacitance which acts as a second plate of a capacitor going to the ground plane, as shown in FIG. 4*b*. Thus, the sensor may be applied to determine whether the sensor is directly touching the skin of the patient or not directly touching the skin of the patient (i.e., a presence of touch or an absence of touch).

The capacitive sensor may also detect its proximity to human skin based on the interaction between human skin and the electric field. Depending on the sensitivity of the capacitive sensor and the range of the electric field, a distance of proximity may be detected.

Each output from a capacitive sensor may be classified based on its strength. For instance, an output having a small strength may suggest an inferior touch or no touch. On the other hand, an output having a great strength may suggest that a touch has occurred or an excessive force has been applied against human skin. Output strengths of a plurality of capacitive sensors may identify areas that have inferior touches as well as areas of excessive force on human skin.

FIG. 5 illustrates a schematic circuit diagram of a capacitive sensor coupled to a processor, such as an Arduino Processor. Each sensor pad may include a send and receive pin. The send pin may have resistors in series. Each resistor $R_{Send}$ may affect how high the output may be at the Serial Port. Each resistor $R_{Send}$ may have a value of 1MΩ. When the capacitive sensor is touched by human skin, the capacitive sensor may produce a result in the range of approximately 1000 units. On the other hand, when no touch occurs, the capacitive sensor may produce an output between 0 and 50 units. Sensitivity of the capacitive sensor may depend on the resistor value. The greater the resistor value, the more sensitive the capacitive sensor.

In one embodiment, the capacitive sensor may have an exposed metal contact area allowing direct contact with a human being, that is, at the surface of the seal of the mask cushion of the patient interface where the seal/sensor will contact a patient's face. In another embodiment, the capacitive sensor may be protected by a layer of insulation which prevents direct contact between the capacitive sensor and the human being. The layer of insulation may reduce a cross-interference between the sensor pad and any external interference from peripheral devices. However, the layer of insulation may reduce the sensitivity of the capacitive sensor. For instance, in the earlier example, when the capacitive sensor covered by a layer of insulation, e.g., a clear plastic of a thickness of 1 mm, is touched by a human being, the capacitive sensor produces an output of approximately 1000 units. Removal of the insulation layer may increase the output up to 3000-4000 units when touched by the human being. Further, without insulation, the capacitive sensor output may fluctuate more often due to increased sensitivity. Thus, in some indirect sensing versions, the sensor may be embedded within a cushion of the patient interface.

The capacitive sensor may be implemented with one or more materials, and may be incorporated in the mask according to one or more different mechanisms. In one example, the capacitive sensor may be made of copper. As illustrated in FIG. 6, a capacitive sensor may include a copper tape 601 exhibiting an oblong shape. The copper tape 601 may have dimensions of approximately 15 mm by 10 mm by 0.06 mm. The copper tape 601 may be attached to either an outer membrane or an inner membrane of the seal-forming structure 3100 of the mask. When the copper tape 601 is attached to the inner membrane of the seal-forming structure 3100, the outer membrane may act as an insulation layer, reducing direct contact between the sensor and human skin.

In another example, one or more capacitive sensors may be weaved into the mask or the seal-forming structure 3100 using conductive thread, resulting in a complete textile mask. As illustrated in FIG. 7, each capacitive sensor 701 may be made of textiles. These sensors may be weaved into the material of the seal-forming structure 3100. Each sensor may include one or more individual conductive paths to transmit information detected by the sensor to a processor.

5.3.10.1.2 Resistive Sensor

In one form, the auto-fit mask may include one or more resistive sensors. A resistive sensor may implement the concept of resistive touch to identify contact, or regions of interaction between the mask and human skin. A resistive sensor may detect contact between human skin and a sensor pad based on a change in resistance. Human skin may act as a conductor of electricity, as current can flow therein between two points of contact. For that reason, human skin may act as an electrical component that contains a resistance. For example, FIG. 8a and FIG. 8b each show a pair of parallel conductive elements that do not touch. As shown in FIG. 8b, when human skin touches the two elements, it creates a bridge that closes the circuit. The more touch there is by the skin, the higher the resistance. Based on the above concept, the resistive sensor output varies depending on whether a touch occurs. When a touch occurs, the resistive sensor may produce a high output measure. In the absence of a touch, the resistive sensor may produce a low output measure (e.g. current). Thus, the sensor may be applied to determine whether the sensor is directly touching the skin of the patient or not directly touching the skin of the patient (i.e., a presence of touch or an absence of touch).

Each resistive sensor may include at least one pair of parallel conductive elements placed on the outer membrane of the mask for direct contact with human skin. No insulation material is placed over the resistive sensor.

FIG. 9 illustrates a schematic circuit diagram of one or more resistive sensors coupled to a processor. In this example, the processor is an Arduino Processor.

Table 1 identifies safe current limits for human contact. In one form, the current applied through the resistive sensor may have a magnitude of approximately 1 mA.

TABLE 1

Current Limitations for Human Touch

| Current | Response |
| --- | --- |
| <1 mA | Barely perceptible |
| 10 mA | Maximum current a 120 lb man can grasp and "let go" |
| 16 mA | Maximum current a 175 lb man can grasp and "let go" |
| 18 mA | Paralysis of respiratory muscles |

As seen in Table 1, currents that may be safely applied to a human body have small magnitudes. For that reason, a processor may incorporate a current amplifier circuit, as shown in FIG. 10, to amplify any current flowing through the resistive sensor. Referring to FIG. 10, R1 may have a value of 100 kΩ. Any change to the resistance value may change sensitivity of the resistive sensor. Transistors used in the current amplifier circuit may be NPN C547. The transistors may provide a gain, $h_{fe}$ of 90-200. The transistors may be configured in a Darlington pair to amplify current at the collector.

The resistive sensor may be implemented with one or more materials, and may be incorporated by the mask according to one or more different mechanisms. For example, a resistive sensor may include at least one pair of parallel touch pads. Each touch pad may include a conductive path therein. A touch pad may exhibit a linear profile, or an "L" shape, among other alternatives. In one example, the resistive sensor may include material coated in conductive paint.

FIGS. 11a and 11b illustrate pairs of parallel touch pads 1101, 1102 arranged in an interlaced or cross-linked fashion. This arrangement has the benefit of increasing the surface area of the resistive sensor available for human touch. This arrangement also has the benefit of reducing gaps between parallel conductive paths.

FIG. 12 illustrates another embodiment of the resistive sensor 1201 having tin-coated copper wire or conductive yarn arranged in an interlaced fashion. In the example shown, the resistive sensor may include pairs of conductive elements. Each conductive element may exhibit an "L" shape. The conductive elements within each pair may face inwardly towards each other, and may be offset laterally from each other.

5.3.10.1.3 Resistive Ink Bend Sensor

In one form, the mask may include one or more resistive ink bend sensors. As shown in FIG. 13, each resistive ink bend sensor 1301 may include a conductive ink. The conductive ink may be printed on either the mask or the seal-forming structure 3100. Alternatively, the conductive ink may be first printed on a plastic film, and the plastic film may be then assembled onto the mask or the seal-forming structure 3100. Each resistance ink bend sensor may be configured to detect bonding, movement, vibration, humidity, and more. The resistance of the ink may vary depending on the extent of deflection of the resistive ink bend sensor. For instance, the resistance may increase as the ink is stretched apart.

Referring to FIG. 13, each ink print may be regarded as one sensor. In one example, an ink painted on one side of the seal-forming structure 3100 may result in a unipolar sensing device. Its resistance increases as the sensor deflects in one direction. No such change in the resistance occurs, when the sensor deflects in the opposite direction.

In another example, the ink may be printed on both the inside and outside of the seal-forming structure 3100, resulting in a bipolar sensing device. The bipolar sensing device includes two sensors that detect deflection in both directions. When the seal-forming structure 3100 is ideally sealed against human skin or in a nominal position, the sensors may output a steady nominal resistance. If the seal-forming structure 3100 is over compressed, the resistance of the ink printed on the outside of the seal-forming structure 3100 may increase to a high value. If the seal-forming structure 3100 is under compressed or hyper-extended, the ink on the inside of the seal-forming structure 3100 may increase in resistance and indicate an imminent leak.

As shown in FIG. 13, one or more resistive ink sensors may transmit detected information to a processor for analysis via one or more conductive paths 1302.

5.3.10.1.4 Shear Sensor

In one form, the mask may include one or more shear sensors. A shear sensor may be a pinch shear force sensor or a miniature integrated shear sensor. Each shear sensor may detect contact or an absence thereof between human skin and the mask by detecting one or more of the following: friction, normal force, normal pressure, shear force, pinch shear force, and lateral and vertical instability. When there is no contact between the human skin and the mask, the shear force is approximately zero. As such, shear force may be relied upon to determine if there is a proper seal between the mask and human skin.

FIG. 14 illustrates an array of shear sensors 1401 placed around the seal-forming structure 3100. The shear sensors

1401 may be placed at typical leak trouble spots, such as eyes, cheeks and chin. The shear sensors 1401 may be attached to the seal-forming structure 3100 by adhesives. Alternatively, the shear sensors 1401 may be co-molded with the seal-forming structure 3100 during manufacture process.

5.3.10.1.5 Piezoelectric Film Sensor

In one form, the mask may include one or more piezoelectric film (PVDF) sensors incorporated in the seal-forming structure 3100. The PVDF sensor may be a piezo electric/electro-active polymer film. The PVDF sensor may detect contact between human skin and the seal-forming structure 3100 by detecting any one of the following: a seal contact pressure, a contact force, bend, and leak such as a localized interface leak flow.

In one form, the mask may include a mixture of piezo sensors with different pole directions to monitor conditions required for automatic fit. For example, to monitor contact force, the piezo film may be poled across the thickness of the film. To monitor bend and leak, one or more sensors may be poled along the length of the film. Poling is accomplished by subjecting the film to intense electric potential during the manufacturing process, upon which the dipoles in the material align. The alignment causes the material to collectively respond to changes in their surroundings and different poling directions will result in different responses. The poling process conditions required for PVDF are an electric field in the order of 20 mV/m and 100 degrees Celsius.

The PVDF sensor may have a piezoelectric effect, such that it may vary its output in proportion to the degree of bending. As illustrated in FIG. 15, when the seal-forming structure is in contact with human skin to form a seal, the PVDF sensor may be bent due to the contact. When the PVDF sensor is in its bending position, the sensor may produce a steady voltage signal. By contrast, when the seal-forming structure does not contact human skin, the PVDF sensor resumes its original position which is less bent than the bending position. In this case, the sensor may produce a small fluctuating voltage signal.

The PVDF sensor may also have a pyroelectric effect, such that it may produce a voltage signal in response to changes in temperature. As shown in FIG. 16, when a piezo film is in intimate contact with human skin, the sensor voltage may stabilize in equilibrium with the skin temperature. In the event when a leak is present between the piezo film and human skin, the loss of contact with the warm skin and the convective cooling effect of the leak flow may cause a decrease in the voltage signal produced by the PVDF sensor.

The PVDF sensor may be monitored at a sampling rate suitable for adequate monitoring of a mask fit situation. For example, the sampling rate may be 10 ms. The PVDF sensor may send its output to a processor, a data acquisition unit such as a Crossbow MDA300CA unit or one of similar or smaller size for analysis.

There may be many benefits for using the PVDF sensor. For example, the PVDF sensor may have a thin profile such that it may be easily incorporated into the seal-forming structure 3100. The PVDF sensor may produce strong electrical signals in proportion to stimulation. Further, the PVDF sensor is relatively inexpensive, and may be easily cleaned and manufactured.

5.3.10.1.6 Other Sensors

Sensors discussed herein above are mere examples. Any necessary or desired additional sensors may be integrated with the mask.

For example, the mask may include one or more microphones to detect vibration and acoustic events. Vibration and acoustic events may often accompany a mask leak. For instance, a leak around the cheek regions may produce a flatus like sound and vibration. A leak near the eye may produce a high pitched squeal. A leak near the chin may produce a roar-like signature. By identifying a vibration or acoustic event, the leak location may be identified.

In another example, an infrared camera (FLIR) may detect leaks at the mask through a contactless method, such as by visualizing air flow. The camera may send a detected signal to the mask wirelessly.

Further, the mask may include other mechanical, electrical, magnetic, electromagnetic, pneumatic, optical sensors or any other suitable sensor to detect a contact or leak between human skin and the mask. For example, the present technology may detect touch by using one or more of the following: a temperature sensor, a chemical sensor, and optics/LED+photodetector. The present technology may detect seal contact pressure by using one or more of the following: an air balloon or bubble wrap like material, and a resilient probe with flow passage. The present technology may detect a localized interface leak flow by incorporating pitot tube arrays in the seal-forming structure. The present technology may detect humidity by incorporating humidity sensors in the mask or the seal-forming structure. The present technology may detect the mask position by any one of optics/front and side cameras and linear variable displacement transducer (LVDT). The present technology may detect muscle twitch/skin reaction (EMG) by electrodes placed in the seal-forming structure. The present technology may detect temperature by any one of the following: a thermistor in airpath, thermistors on the seal-forming structure, thermistors touching face, thermal imaging cushion and thermal imaging of skin. The present technology may also detect blood perfusion, red marks or discomfort by transcutaneous oximetry or tissue hypoperfusivity. The present technology may detect tube or flow generator flow by any one of the following: thermistor in airpath, microturbine, and pyroelectric effect of piezo film. The present technology may detect mask air pressure by a pressure sensor. The present technology may detect mask gravitational orientation by either a solid state gyro/accelerometer or a liquid metal (mercury) switch, or a combination thereof. The present technology may detect noise or acoustic events by one or more microphones placed in the flow generator or the seal-forming structure.

Still further, the present technology may predict a likelihood of a leak by performing a sensor sweep. The present technology may include magneto/electro rheological fluid in the seal-forming structure for purposes of adjusting the mask. The present technology may also include photoluminescence to enable interaction with a human being. Further, the present technology may also incorporate one or more of the following sensors: oximeter, EMG, glucometer, strain sensor, and a sensor that may detect flow based leak detection.

5.3.10.1.6 Cushion as Sensor

In some cases, the seal forming portion of a patient interface, such as a cushion or portions thereof, may be implemented as a sensor. For example, the cushion may be implemented as one or more force sensitive sensors along the perimeter of the cushion. In one such version, each sensor may include a foam cushion portion of the seal forming portion. The foam cushion portion may have first and second electrodes (e.g., pairs of electrodes) with a conductive foam cushion between the electrodes. The compression and decompression of the particular conductive foam cushion portion residing between electrode pairs may produce different measurable electrical characteristics across the foam between the electrodes, e.g. resistance changes. For example, compression may decrease the resistance and decompression may increase the resistance. Such changes may then be detected and/or measured with a measuring/processing circuit (e.g., including a processor) coupled with the electrode pairs. In some cases, the electrodes may be formed by thin film conductors, such as an adhesive copper tape. Optionally, the conductive foam may be an open cell foam formed of polyurethane with conductive fibers. Other materials may also be implemented.

Such sensor may be implemented to detect contact of the cushion with the patient's face through the detection of compression (e.g., reduced resistance relative to an uncompressed cushion).

Advantageously, the use of conductive foam and other force sensors may allow force threshold limits to be utilised (e.g., to avoid overtightening of headgear) and allows altering the direction of headgear tension vectors to an optimal vector. Altering the direction of headgear tension vectors allows the mask to seal in an optimal position against the patient's face using the minimum of headgear tension force required thereby improving comfort and minimising the possibility of red marks forming on the patient's face. If the headgear tension vector can't be altered then tightening it may not ideally correspond to improving the seal and stability because it is tightening the mask against the patient's face in the less preferred location(s). For example, a processing system may measure the force at various locations around the periphery of the seal forming portion of the patient interface via the electrode pairs and conductive foam, compare the measurements to one or more thresholds and generate output to the user to report whether the mask generally (or particular straps associated with different ones of the sensors) is too tight or too loose for use. Optionally, such a detection process may serve as control input(s) for automated control of headgear tension or the mask such as for making adjustments to different headgear straps that have automated adjusting components or for making automated adjustments with other actuators of the mask (e.g., of the cushion) as described in more detail herein.

5.3.10.2 Processor

The present technology may include one or more processors to process readings obtained from one or more sensors. For instance, to identify if the mask is in contact with human skin or if there is a leak between them, one or more sensors may send their readings or measured signals to one or more processors for analysis.

FIG. 17 illustrates a system 1700 according to one aspect of the present technology that includes a processor 1701. The processor 1701 may have multiple input/output pins to support numerous sensors 1702. The system 1700 may include a power source 1703, such as a 5V DC battery. The system 1700 may include a display 1704. The display 1704 may be either a voltmeter or a computer interface, such as a Serial Monitor of an Arduino Program.

In one example, one or more sensors may communicate with a signal interface of a processor of a stand-alone monitoring device or a controller of a flow generator that monitors the sensors. Optionally, the sensors may even be configured to communicate with a measurement processor which in turn relays the data collected from the sensors to a processor for signal analysis.

The sensors may generate signals for a controller/detection processor of a monitor or other apparatus by communicating the signals in wire leads to the signal interface of a controller or processor. However, in some embodiments, the sensors themselves may be implemented with components for transmitting the signals to the controller or detection processor by various forms of communication, including wireless. For example, the signals interface of the detection processor or controller may include a receiver or transceiver to communicate wirelessly with one or more transmitters or transceivers integrated with the sensors. In such a case, data representing the signal(s) may be transmitted digitally, for example, by any suitable wireless protocol, such as Bluetooth. Optionally, a set of sensors may share a common transmitter or transceiver for transmission of the data of several sensors to the controller.

The signal(s) produced by these sensors may then be processed by the detection processor to detect leakage. A processor may be configured to implement particular methodologies to detect leakage based on the signals and analysis thereof such as by the algorithms described in more detail herein. For example, a device controller or processor may include integrated chips, such as application specific integrated chip(s), a memory and/or other control instruction, and data or information storage medium with the methodologies. Thus, programmed instructions encompassing the methodologies may be coded on integrated chips or in the memory of the device. Such instructions may be loaded as software or firmware using an appropriate data storage medium.

In some embodiments, signals of the sensors may be analyzed by a processor. In some such embodiments, the signals may be compared to one or more thresholds which may be chosen or derived to identify leakage. Such a threshold value may be determined at the time that a clinician configures the apparatus for patient use. Still further, threshold values may be empirically determined. The threshold attributable to the measurements of any particular sensor may not be a constant value; rather it may be a dynamic value that varies with different circumstances.

In one form, the processor may be part of a controller. The controller may include one or more processors. The controller may be part of, or independent from, a respiratory treatment apparatus. The controller may include one or more processors. The controller may also typically include one or more memory/data storage components containing control instructions of the aforementioned methodologies. These may include processor control instructions, e.g., processor control instructions for signal measuring and processing. They may include stored data associated with executing or processing the data.

In some embodiments, these processor control instructions and data for controlling the above described methodologies may be contained in a computer readable recording medium as software for use by a general purpose computer so that the general purpose computer may serve as a specific purpose computer according to any of the methodologies discussed herein upon loading the software into the general purpose computer.

In one form, when the processor determines that the mask is properly sealed to the patient's skin, the processor may automatically instruct a flow generator to start supplying breathable gas to the patient. In the event that the mask is not properly sealed to the patient's skin, the processor may automatically instruct the flow generator to stop supplying breathable gas to the patient.

The processor may incorporate tools such as a high pass filter to detect and filter high frequency oscillations in sensor readings.

Specific embodiments of one or more processors for processing readings provided by different sensors are described herein.

5.3.10.2.1 Process Capacitive Sensor Output

A processor may process one or more readings provided by one or more capacitive sensors. In one form, the processor may be an Arduino Mega2560 Board.

An example methodology for such a processor to assess a signal generated by a capacitive sensor is illustrated in the flow chart of FIG. 18. At 1801, the processor may determine whether the sensor is on. If yes, the processor may determine if the sensor is on the skin at 1802. If yes, the processor may determine at 1803 that the mask is on the skin, in which case the processor may instruct to display a message "Mask right side is on." If the sensor is not on the skin, the processor may determine at 1804 if the skin is close to the sensor. If yes, the processor may determine that the mask is potentially ill-fit at 1805, in which case the processor may instruct to display a message "Potential mask ill-fit." If the skin is not close to the sensor, the processor may determine at 1806 if the skin is on to the sensor. If no, the processor may determine that the mask is off the skin at 1807, in which case the processor may instruct to display a message "Mask right side is off"

5.3.10.2.2 Process Resistive Sensor Output

A processor may process one or more readings provided by one or more resistive sensors. In one form, the processor may be an Arduino Uno Board.

An example methodology for such a processor to assess a reading provided by a resistive sensor is illustrated in the flow chart of FIG. 19. After power is turned on at 1901, the processor may determine at 1902 whether the reading provided by the resistive sensor is above a first threshold. If yes, the processor may determine that the mask is on the skin at 1903, in which case the processor may instruct to display a message "Mask is on" or generate an alert to report the same. If the reading output by the resistive sensor is not above the threshold, the processor may determine at 1904 whether the reading is below a second threshold. If yes, the processor may determine that the mask is off the patient's skin at 1905, in which case the processor may instruct to display a message "Mask is off" or generate an alert to report the same. The first threshold and the second threshold may be identical, or different from each other.

5.3.10.2.3 Process Shear Sensor Output

A processor may process one or more readings provided by one or more shear sensors. In one form, the processor may be an Atmega128L or any other suitable processor.

An example methodology for a processor to assess a reading provided by a shear sensor is illustrated in the flow chart of FIG. 20. At 2001, the processor may obtain the reading from the shear sensor. The reading may be taken of the normal and shear forces. At 2002, the processor may determine if the normal force is greater than a first predetermined threshold. The first predetermined threshold may be zero. If the normal force is not greater than the first predetermined threshold, then at 2003, the processor may determine that the sensor is off the skin and a leak has occurred. At 2004, the processor may issue a command to tighten an appropriate strap. Thereafter, the processor may obtain a new reading from the shear sensor at 2001 and repeat the above analysis.

If the normal force is greater than the first predetermined threshold, then the processor may determine that the sensor is on the skin. At 2005, the processor may compare an absolute value of a shear force reading to a second predetermined threshold. Lateral shear forces may be caused by interferences with the mask, such as air delivery tubing drag or bedding interferences. The second predetermined threshold may be a pre-defined limit where the mask is known to be destabilized. In one example, the second predetermined threshold may be zero. If the lateral shear exceeds the second predetermined threshold, this may be an indication of destabilized mask. If the threshold is not exceeded, the processor may determine at 2006 that the mask is stable, and proceed to read the next senor. However, if this threshold is exceeded, the processor may determine the direction of the force at 2007, and issue an appropriate command to a strap tension system. For instance, if the force vector is outward, the processor may determine that leak is imminent on the opposite side, and instruct to tighten nearest straps at 2008. If the force vector is not outward, then the processor may determine that leak is imminent on the near side and instruct to tighten an opposing strap at 2009. For example, if the shear force vector on the cheek portion of the cushion points laterally away from the face, then the strap on the same side may be commanded to tighten to pull the mask back into alignment. This is the scenario where a patient turns his or her head sideways and digs the mask into the pillow causing it to be displaced sideways. The same principle may be applied to the vertical vectors and displacements.

5.3.10.3 Reactive or Adjusting Component

If one or more processors discussed above determine that the mask is not properly sealed against human skin or that there is likely a loss of seal, the mask may automatically adjust itself to prevent the loss of seal or stop leakage. In one form, the present technology may include one or more reactive or adjusting components to adjust the mask to maintain an optimum seal with a user. The reactive or adjusting components may have various embodiments. For example, the reactive or adjusting components may include piezoresistive fabric for purposes of automatically maintaining a desired headgear tension level without user interaction. In another example, the reactive or adjusting components may include actuators or motors to adjust headgear straps. Alternatively, the reactive or adjusting components may include shape-changing material in the seal-forming structure 3100 such that the structure 3100 may change its shape or geometry under various circumstances such as in response to an application of electrical signal or a temperature change. In another example, the reactive or adjusting components may include shape memory alloys, such as nitinol, or other materials suitable for diffusionless or martensitic transformation. Details of some embodiments of the reactive or adjusting components are discussed herein.

In some versions, a processor may directly detect touch, such as with a capacitive or resistive sensor. In one type of an on/off detection scenario, when there is an absence of a direct touch signal, the actuators may be controlled by the processor to adjust until it detects a direct touch signal and then stop. Therefore, it could close a leak. To detect overtightening headgear scenarios, the actuators may be controlled by a processor to adjust to loosen until the processor detects an absence of direct touch signal, and then increment to tighten by a small amount until it detects a direct touch signal and then stop. This control methodology could achieve a seal with optimum comfort (i.e., the least amount of force required to maintain a seal). In alternative versions, the processor may control an actuator to make changes based on detecting a rate of change of strain/distance with suitable sensors.

5.3.10.3.1 Piezoresistive Fabric Headgear

The present technology may measure and maintain a consistent and desired headgear tension without any user interaction. In one form, one or more headgear straps may include smart textiles. The smart textiles may contain piezoresistive properties. When the headgear is adjusted, such as tightened or loosened, its tension may be measured and analyzed to determine whether the headgear strap is too tight or too loose. If there are areas of excessive strain along the headgear strap, the headgear straps may be automatically adjusted to reduce its tension without any user interaction.

In one form, the smart textiles may include piezoresistive fabric. The piezoresistive fabric may have a high sensitivity to detect stress or tension. The piezoresistive fabric may have an electrical resistivity which changes as a result of an amount of mechanical stress applied. Stress may cause a change in the mobility and number of charge carriers within a material. As a result, when stress is applied, the resistance across a distance of the fabric may increase.

The piezoresistive fabric may be implemented in one or more straps of the headgear. For example, one or more straps of the headgear may be near the patient's chin and/or mouth. Tensions in the straps may vary due to the patient's movement, and may also vary depending on whether the mask is properly sealed against the patient's skin.

FIG. 21 illustrates an example headgear strap 2100 implemented with smart textiles. In this example, the smart textiles may include eeonyx piezoresistive fabric 2150. The fabric 2150 may be cut into the shape as shown in FIG. 22. The strap 2100 may include two probes, namely, a left hand side probe 2101 and a right hand side probe 2102, configured to measure a resistance across the material. Each probe may include a conductive strip disposed laterally across the material. Each conductive strip may have a conductive path, such as an insulated wire 2103, 2104 coupled to a PCB board 2105. To reduce any discomfort to the user as well as to go unnoticed, the wires 2103, 2104 may be encased and concealed within a cavity 2106 sewn into the strap 2100. The cavity 2106 may be used for both the right side and left side of the strap 2100.

The strap 2100 may include a clip or material feeder 2107 to adjust the length of the fabric 2150. The fabric 2150 and clip 2107 may be easily removed from the headgear to facilitate cleaning the mask.

The PCB 2105 may be mounted on one side of the clip 2107. A motor may be included to automatically feed or extract material through the clip 2107 based on instructions from the PCB 2105. A battery holder may exist between the clip and the PCB 2105 to receive a battery therein. The battery holder may have dimensions approximately 25 mm by 20 mm.

FIG. 23 illustrates an example system architecture where results of the left hand side probe 2101 and the right hand side probe 2102 may be transmitted to a processor 2301, such as the PCB 2105 illustrated in FIG. 21, for analysis. A battery 2302 may be used as a power source for the processor. The battery 2302 may be a Lithium cell or button cell. The battery may have a supply of at least 3.0V.

Information obtained from the two probes may be transmitted to the processor and interpreted by the processor. The processor may communicate with the user to highlight any potential issues such as the headgear strap is too tight or too loose. An example methodology for such a processor is illustrated in the flow chart of FIG. 24. At 2401, the processor may read a measurement between the left probe and the right probe. The processor may determine tension in the headgear strap based on the measurement. At 2402, the processor may determine if the strap is too tight. If yes, the processor may at 2403 instruct to display a message that the strap is too tight. The processor may send instructions to adjust the strap to reduce its tension. If the strap is not too tight, the processor may at 2404 determine if the strap is too loose. If yes, the processor may at 2405 instruct to display a message that the strap is too loose. The processor may send instructions to adjust the strap to increase its tension. If the strap is not too loose, the processor may continuously determine at 2406 if the strap is too tight. If yes, the processor may instruct to display a message that the strap is too tight. The processor may send instructions to adjust the strap to reduce its tension. The processor may return to step 2402 to continue analysis.

As discussed above, once the processor processes the signals obtained from the probes, the processor may adjust the tension in the headgear strap to an acceptable level. For instance, if the headgear strap is too tight, the strap may be loosened by feeding more material through the clip 2107 to increase the length of the strap. If the headgear strap is too loose, the strap may be tightened by extracting material through the clip 2107 to reduce the length of the strap.

5.3.10.3.2 Nylon Filament and Heater Filament

In one form of the present technology, the headgear may include artificial muscles to maintain an optimal seal between the mask and human skin. The artificial muscles may extend or contract as needed. In one example, the artificial muscles may include one or more of the following: a nylon filament and a heater filament.

In one form, the artificial muscles may be formed from nylon filaments that are twisted into a coil in conjunction with a flexible low power heating element. Alternatively, the fiber may be metal coated by an electroless plating process. When heated by the element, the coil assembly may contract by as much as 50% of its starting length. Multiple muscles may be joined in parallel and interwoven with a comfortable headgear material to produce the desired amount of force and elasticity. If additional movement is needed, the muscle assemblies may be joined in series.

There are many advantages for implementing the artificial muscles with the nylon filament and the heater filament. For instance, these filaments are significantly cheaper, lighter, less complicated and easier to be incorporated into the headgear than most other actuator systems such as shape memory alloy actuator material, stepper motors and pneumatic actuators. For example, shape memory alloy actuator material can cost as much as $3000 per kilogram, posing a significant barrier to actual commercialization, whereas nylon filament can cost as little as $5 per kilogram. Shape memory alloys may also pose a skin irritation hazard due to its nickel and copper content. Pneumatic actuators also have flaws. For instance, there may be differences between the actuator's required operating pressures and the available pressure used for therapy. As such, pneumatic actuators require added complexity such as a gas pressure regulator or additional pump.

Further, the artificial muscles disclosed herein may obviate any need for Velcro tabs, which may otherwise cause difficulty for CPAP users. With multiple combinations and configurations of the artificial muscles, it may be possible to have a headgear that is loose or elastic enough in a de-energized state, such that it does not need to be unclipped or disassembled during donning, eliminating a major frustration of CPAP therapy. Instead, the wearer may simply don a fully assembled mask, activate the therapy and have the straps automatically contract to the optimal length and tension.

5.3.10.3.3 Cushion Actuator

In one form, the present technology may include electro active elements such as PVDF piezoelectric films on the mask. The electro active elements may be attached or molded in an outer membrane of the seal-forming structure 3100. These actuators may have an inverse-piezo effect which converts electrical stimulus into physical movement, thereby blocking any air leaks between the mask and human skin.

In one form, the electro active elements may be attached to the inside of the seal-forming structure 3100. These elements may be disposed within the seal-forming structure 3100 at a position such that when de-energized, the electro active elements may form a nominal cushion shape profile, such as a "C" shape profile. If a leak is detected between the mask and human skin, the piezo actuator in the immediate vicinity of the leak location may be energized with a charge so that the piezo actuator may straighten and unfurl the seal-forming structure towards the human skin, thereby stemming the leak.

The amount of force exerted on the human skin may be periodically adjusted by rotating the application of charges to one or more electro active elements at multiple cushion regions, thereby making the mask more comfortable for prolonged use.

ResMed WO 2013/067582 A1 discloses electro-active cushion elements and also discloses periodically cycling force around the cushion to enable the mask to be worn for a prolonged time, the entirety of which is incorporated herein by reference.

5.3.10.3.4 Other Reactive or Adjusting Components

In addition to the examples provided above, the present technology may include other reactive or adjusting components to automatically adjust the mask to maintain an optimal seal with human skin.

For example, to adjust tension in a headgear strap, the present technology may include one or more of the following: shape memory alloy, pneumatic or hydraulic airbag or bladder, and stepper motor. To prevent or eliminate leaks between the mask and human skin, the seal-forming structure may include shape changing materials, such as electro-rheological fluid, magneto-rheological fluid, pneumatic or hydraulic airbag or bladder, humidity shape changing material, and electro active polymer or elastomer. Similarly, the mask frame may include one or more of the following materials: yielding material, solenoid, pneumatic or hydraulic airbag or bladder and electro active polymer. To adjust orientation of the mask, a torque motor may be included to tilt or balance the mask. Further, to simplify donning and removal of the headgear, the headgear may include a rapid release system to release the headgear tension elements.

5.3.10.4 Prediction System

In one form, the present technology may include a prediction system that predicts the likelihood of a leak between the mask and human skin. If a loss of seal is likely to occur, the prediction system may instruct one or more reactive or adjusting components to automatically adjust the mask prior to an actual loss of seal. The prediction system may predict a leak based on continuous monitoring of one or more of the following: force sensor, pressure sensor such as seal contact pressure sensor, shear and friction sensors, orientation sensor, position sensor, duration monitoring, transcutaneous oximetry, and tissue hypoperfusivity. Based on one or more of the monitored features, the prediction system may predict an imminent leak. The prediction system may also analyze one or more of the monitored features to detect an onset of red marks or patient discomforts. If such an onset is detected, a leak may be predicted to occur in a distant future, if not sooner.

FIG. 25 illustrates an example methodology processed by the prediction system. At 2501, the prediction system may obtain one or more readings from one or more sensors such as force, pressure, seal contact pressure, shear and friction sensors. The prediction system may compare one or more readings to a first threshold. The first threshold may be a value at which a leak or other detrimental mask events are statistically known to occur, plus a safety factor. Next, the prediction system may compute a rate of change of the sensor readings. At 2502, the prediction system may compare the rate of change of the sensor output to a second threshold. If the rate of change exceeds the second threshold, the prediction system may determine at 2503 that the loss of seal is likely to occur. As a result, the prediction system may initiate an appropriate preventative action, such as tightening a headgear strap.

FIG. 26 illustrates another example methodology processed by the prediction system. The prediction system may monitor lag instruments. In this example, at 2601, the prediction system may read an orientation signal obtained from an orientation sensor. At 2602, the prediction system may determine whether the patient is shifting based on the orientation signal. If the patient is not shifting, the prediction system may continuously monitor output by the orientation sensor at 2601 and repeat the above analysis. If the patient is shifting, the prediction system may at 2603 take an appropriate action to compensate for orientations known to increase the likelihood of leak. For instance, the prediction system may instruct one or more reactive or adjusting components to tighten a bottom headgear strap.

FIG. 27 illustrates yet another example methodology processed by the prediction system. In this example, at 2701, the prediction system may obtain skin oxygen levels from an oximeter. At 2702, the prediction system may determine if any sensor has registered hypoperfusion (lack of blood flow due to the seal-forming structure 3100 crushing the skin). If no sensor has registered hypoperfusion, the prediction system may at 2703 wait 15 minutes and loosen to point of leak. The prediction system may loosen periodically to allow re-perfusion all round. If a sensor has registered hypoperfusion, the prediction system may at 2704 loosen the nearest strap. Thereafter, the prediction system may continuously or periodically read the skin oxygen levels and repeat the above analysis.

5.3.10.5 Learning System

In one form, the present technology may include a learning system that learns how to fit the mask to a patient's skin. The learning system may integrate a learning behavior into a processor for the mask. The learning system may learn a patient's prior, preferred or most used settings upon donning. The learning system may store the prior settings in a solid state memory. These settings may include parameters relevant to the fitting of the mask to the patient's skin. For instance, these settings may include strap length, position, force, pressure, position, tilt angles and mask shape. The learning system may store time histories of these parameters, and statically process the time histories of these parameters for reference purposes upon next donning. The learning system may analyze trends of these parameters, and perform data log analysis to develop an optimal setting for fitting the mask to the patient.

In one form, the learning system may record the amount of force required to seal the mask to the patient's face over three nights. The average value may be adopted by the processor on subsequent sessions, and an optimization routine may run thereafter. If a mask has never been worn before, then a regular fitting routine may run first.

An example methodology for determining how to fit a mask to a patient is illustrated in the flow chart of FIG. 28.

At 2801, a system may determine if the mask has been used or fitted before. If no, at 2802, the system may run a fitting routine. At 2803, the system may run routines to predict leakage and adjust the mask to an optimal sealing position, for example, according to algorithms described in FIGS. 25-27. However, if the mask has been used or fitted before, the system may at 2804 load previous settings associated with the mask. For example, these previous settings may include some of the most used settings for applying the mask to a patient, including strap positions 2810, force 2812, pressure 2814, position/orientation 2816 and shape 2818. Thereafter, at 2820, the system may open the straps to make them ready for fitting. At 2830, the system may fit the mask to the patient. At 2840, the system may adopt an optimal setting developed based on the previous settings by the learning system. At 2850, the system may run routines to predict leakage and adjust the mask to an optimal sealing position, for example, according to algorithms described in FIGS. 25-27.

Although the mask has a procedure and ability to fit and conform to the patient's face automatically, the learning system may minimize the amount of time and fuss taken to achieve a perfect fit. As such, the learning system may ultimately improve the ease and speed to start CPAP therapy as well as improve the compliance rate of CPAP therapy.

5.3.10.6 Alert

In one form, the present technology may generate one or more alerts upon detection of a leak or lack of seal between the mask and human skin. For example, when such a device determines that a leak or lack of a touch, the device can be programmed to provide a warning or message in a form suitable for the patient or clinicians. For instance, alerts may be provided to the patient or the patient's partner in a discrete manner, or sent to the patient at a later time such as the next morning. Alerts may be sent to a clinician via cloud computing. In some instances, alerts regarding the operation of the device may be sent to a device manufacture via cloud computing.

The warning or messaging of the system may take a number of forms. For example, the processor or a controller with such a processor, in response to analysis of the leakage detection signal, may activate a status light (e.g., an LED or an icon on a display screen or LCD) of the monitoring device. By way of example, multicolor LED lights may be used, where certain colors portray corresponding alerts. As an example, a green LED may signify comfortable tension, and a red LED may represent the headgear being too tight. Depending on what the power source is and the processing power, the output may even be a wireless function to the Flow Generator that would appear as "Mask Fit."

A more detailed message concerning the assessment of the indicator may also be displayed on the display screen. The detailed message may include event detection reports, results or graphs, or warnings. An example embodiment of a display or warning that may be presented to a patient or physician by the device may be a warning message such as a graphic or textual message advising of misplacement of the mask. The message may be displayed on the device or a remote device. Such a message may take the form of a wired or wireless communication. For example, the controller may generate a message via a paging system such as by automatically dialing a paging system. The controller may also be configured to generate an automated voice phone call message. The controller may also send the message by a fax transmission. In some embodiments, the controller may also send a message via any internet messaging protocol, such as an email message, or by any other internet data file transport protocol. The messages may even been encrypted to keep patient information confidential. A typical message may identify the patient. Such a message may also include the data of the changes recorded by the system and/or any other recorded patient information. Optionally, the warning may be an audible alarm.

5.3.10.7 Power/Energy

In one form, the present technology may rely on one or more power or energy sources to power the components described herein. Example power sources and means for providing power may include, but not limited to, solid state battery, energy harvesting (bio energy harvesting), wireless power, microturbine, RF (wireless power), induction coupling, and wire connections.

5.4 RPT Device 4000

A preferred RPT device 4000 in accordance with one aspect of the present technology comprises mechanical and pneumatic components 4100, 4020, electrical components 4200 and is configured to execute one or more algorithms 4300. The RPT device preferably has an external housing 4010, preferably formed in two parts, an upper portion 4012 and a lower portion 4014. Furthermore, the external housing 4010 may include one or more panel(s) 4015, 4202 and 4210. Preferably the RPT device 4000 comprises a chassis 4016 that supports one or more internal components of the RPT device 4000. The RPT device 4000 may include a handle 4018 and upper portion housing component 4220.

The pneumatic path of the RPT device 4000 preferably comprises one or more air path items, e.g. an inlet air filter 4112, an inlet muffler 4122, a pressure generator 4140 capable of supplying air at positive pressure (preferably a blower 4142), an outlet muffler 4124 and one or more transducers 4270, such as pressure sensors 4272 and flow sensors 4274.

5.5 Humidifier 5000

5.5.1 Humidifier Overview

In one form of the present technology there is provided a humidifier 5000 (e.g. as shown in FIG. 5a) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

5.6 Glossary

For the purposes of the present technology disclosure, in certain forms of the present technology, one or more of the following definitions may apply. In other forms of the present technology, alternative definitions may apply.

5.6.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g. acoustic) noise may be considered to be the background noise level in the room where a patient is located, other than for example, noise generated by a RPT device or emanating from a mask or patient interface. Ambient noise may be generated by sources outside the room.

Continuous Positive Airway Pressure (CPAP): CPAP treatment will be taken to mean the application of a supply of air to the entrance to the airways at a pressure that is continuously positive with respect to atmosphere, and preferably approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example being increased in response to detection of indications of partial upper airway obstruction, and decreased in the absence of indications of partial upper airway obstruction.

5.6.2 Aspects of the Respiratory Cycle

Apnea: Preferably, apnea will be said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): Preferably breathing effort will be said to be the work done by a spontaneously breathing person attempting to breathe.

Expiratory portion of a breathing cycle: The period from the start of expiratory flow to the start of inspiratory flow.

Flow limitation: Preferably, flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:
(i) Flattened: Having a rise followed by a relatively flat portion, followed by a fall.
(ii) M-shaped: Having two local peaks, one at the leading edge, and one at the trailing edge, and a relatively flat portion between the two peaks.
(iii) Chair-shaped: Having a single local peak, the peak being at the leading edge, followed by a relatively flat portion.
(iv) Reverse-chair shaped: Having a relatively flat portion followed by single local peak, the peak being at the trailing edge.

Hypopnea: Preferably, a hypopnea will be taken to be a reduction in flow, but not a cessation of flow. In one form, a hypopnea may be said to have occurred when there is a reduction in flow below a threshold for a duration. A central hypopnea will be said to have occurred when a hypopnea is detected that is due to a reduction in breathing effort. In one form in adults, either of the following may be regarded as being hypopneas:
(i) a 30% reduction in patient breathing for at least 10 seconds plus an associated 4% desaturation; or
(ii) a reduction in patient breathing (but less than 50%) for at least 10 seconds, with an associated desaturation of at least 3% or an arousal.

Hyperpnea: An increase in flow to a level higher than normal flow.

Inspiratory portion of a breathing cycle: Preferably the period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow (Qpeak): The maximum value of flow during the inspiratory portion of the respiratory flow waveform.

Respiratory flow, airflow, patient airflow, respiratory airflow (Qr): These synonymous terms may be understood to refer to the RPT device's estimate of respiratory airflow, as opposed to "true respiratory flow" or "true respiratory airflow", which is the actual respiratory flow experienced by the patient, usually expressed in litres per minute.

Tidal volume (Vt): The volume of air inhaled or exhaled during normal breathing, when extra effort is not applied.

(inhalation) Time (Ti): The duration of the inspiratory portion of the respiratory flow waveform.

(exhalation) Time (Te): The duration of the expiratory portion of the respiratory flow waveform.

(total) Time (Ttot): The total duration between the start of the inspiratory portion of one respiratory flow waveform and the start of the inspiratory portion of the following respiratory flow waveform.

Typical recent ventilation: The value of ventilation around which recent values over some predetermined timescale tend to cluster, that is, a measure of the central tendency of the recent values of ventilation.

Upper airway obstruction (UAO): includes both partial and total upper airway obstruction. This may be associated with a state of flow limitation, in which the level of flow increases only slightly or may even decrease as the pressure difference across the upper airway increases (Starling resistor behaviour).

Ventilation (Vent): A measure of the total amount of gas being exchanged by the patient's respiratory system, including both inspiratory and expiratory flow, per unit time. When expressed as a volume per minute, this quantity is often referred to as "minute ventilation". Minute ventilation is sometimes given simply as a volume, understood to be the volume per minute.

5.6.3 RPT Device Parameters

Flow rate (or flow): The instantaneous volume (or mass) of air delivered per unit time. While flow rate and ventilation have the same dimensions of volume or mass per unit time, flow rate is measured over a much shorter period of time. In some cases, a reference to flow rate will be a reference to a scalar quantity, namely a quantity having magnitude only. In other cases, a reference to flow rate will be a reference to a vector quantity, namely a quantity having both magnitude and direction. Where it is referred to as a signed quantity, a flow rate may be nominally positive for the inspiratory portion of a breathing cycle of a patient, and hence negative for the expiratory portion of the breathing cycle of a patient. Flow rate will be given the symbol Q. Total flow, Qt, is the flow rate of air leaving the RPT device. Vent flow, Qv, is the flow rate of air leaving a vent to allow washout of exhaled gases. Leak flow, Ql, is the flow rate of unintentional leak from a patient interface system. Respiratory flow, Qr, is the flow rate of air that is received into the patient's respiratory system.

Leak: Preferably, the word leak will be taken to be a flow of air to the ambient. Leak may be intentional, for example to allow for the washout of exhaled $CO_2$. Leak may be unintentional, for example, as the result of an incomplete seal between a mask and a patient's face. In one example leak may occur in a swivel elbow.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes in the patient interface.

Pressure: Force per unit area. Pressure may be measured in a range of units, including $cmH_2O$, $g$-$f/cm^2$, hectopascal. 1 $cmH_2O$ is equal to 1 $g$-$f/cm^2$ and is approximately 0.98 hectopascal. In this specification, unless otherwise stated, pressure is given in units of $cmH_2O$. The pressure in the patient interface is given the symbol Pm, while the treatment pressure, which represents a target value to be achieved by the mask pressure Pm at the current instant of time, is given the symbol Pt.

Sound Power: The energy per unit time carried by a sound wave. The sound power is proportional to the square of sound pressure multiplied by the area of the wavefront. Sound power is usually given in decibels SWL, that is, decibels relative to a reference power, normally taken as $10^{-12}$ watt.

Sound Pressure: The local deviation from ambient pressure at a given time instant as a result of a sound wave travelling through a medium. Sound pressure is usually given in decibels SPL, that is, decibels relative to a reference pressure, normally taken as $20 \times 10^{-6}$ Pascal (Pa), considered the threshold of human hearing.

5.6.4 Terms for Ventilators

Adaptive Servo-Ventilator: A ventilator that has a changeable, rather than fixed target ventilation. The changeable target ventilation may be learned from some characteristic of the patient, for example, a respiratory characteristic of the patient.

Backup rate: A parameter of a ventilator that establishes the minimum respiration rate (typically in number of breaths per minute) that the ventilator will deliver to the patient, if not otherwise triggered.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

EPAP (or EEP): a base pressure, to which a pressure varying within the breath is added to produce the desired mask pressure which the ventilator will attempt to achieve at a given time.

IPAP: desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the minimum value during expiration (e.g., PS=IPAP−EPAP). In some contexts pressure support means the difference which the ventilator aims to achieve, rather than what it actually achieves.

Servo-ventilator: A ventilator that measures patient ventilation has a target ventilation, and which adjusts the level of pressure support to bring the patient ventilation towards the target ventilation.

Spontaneous/Timed (S/T)—A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the respiratory portion of the breathing cycle by the patient's efforts.

Ventilator: A mechanical device that provides pressure support to a patient to perform some or all of the work of breathing.

5.6.5 Anatomy of the Face

Ala: the external outer wall or "wing" of each nostril (plural: alar)

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfurt horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Lip, lower (labrale inferius):

Lip, upper (labrale superius):

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear) dividing the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramentale: The point of greatest concavity in the midline of the lower lip between labrale inferius and soft tissue pogonion 5.6.6 Anatomy of the Skull Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

5.6.7 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.6.8 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, a preferred form of LSR has a Shore A (or Type A) indentation hardness in the range of about 35 to about 45 as measured using ASTM D2240

Polycarbonate: a typically transparent thermoplastic polymer of Bisphenol-A Carbonate.

5.6.9 Aspects of a Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: A conduit that directs an axis of flow of air to change direction through an angle. In one form, the angle may be approximately 90 degrees. In another form, the angle may be less than 90 degrees. The conduit may have an approximately circular cross-section. In another form the conduit may have an oval or rectangular cross-section.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. Preferably the headgear comprises a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls enclosing a volume of space, the volume having air therein pressurised above atmospheric pressure in use. A shell may form part of the walls of a mask plenum chamber.

Seal: The noun form ("a seal") will be taken to mean a structure or barrier that intentionally resists the flow of air through the interface of two surfaces. The verb form ("to seal") will be taken to mean to resist a flow of air.

Shell: A shell will be taken to mean a curved two-dimensional structure preferably having bending, tensile and compressive stiffness, for example, a portion of a mask that forms a curved structural wall of the mask. Preferably, compared to its overall dimensions, it is relatively thin. In some forms, a shell may be faceted. Preferably such walls are airtight, although in some forms they may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel: (noun) A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. Preferably there is little or no leak flow of air from the swivel in use.

Tie: A tie will be taken to be a structural component designed to resist tension.

Vent: (noun) the structure that allows an intentional flow of air from an interior of the mask, or conduit to ambient air, e.g. to allow washout of exhaled gases.

5.6.10 Terms Used in Relation to Patient Interface

Curvature (of a surface): A region of a surface having a saddle shape, which curves up in one direction and curves down in a different direction, will be said to have a negative curvature. A region of a surface having a dome shape, which curves the same way in two principal directions, will be said to have a positive curvature. A flat surface will be taken to have zero curvature.

Floppy: A quality of a material, structure or composite that is one or more of:

Readily conforming to finger pressure.
Unable to retain its shape when caused to support its own weight.
Not rigid.
Able to be stretched or bent elastically with little effort.

The quality of being floppy may have an associated direction, hence a particular material, structure or composite may be floppy in a first direction, but stiff or rigid in a second direction, for example a second direction that is orthogonal to the first direction.

Resilient: Able to deform substantially elastically, and to release substantially all of the energy upon unloading, within a relatively short period of time such as 1 second.

Rigid: Not readily deforming to finger pressure, and/or the tensions or loads typically encountered when setting up and maintaining a patient interface in sealing relationship with an entrance to a patient's airways.

Semi-rigid: means being sufficiently rigid to not substantially distort under the effects of mechanical forces typically applied during positive airway pressure therapy.

5.7 Other Remarks

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology.

The invention claimed is:

1. A patient interface for sealed delivery of a flow of breathable gas to a patient's airway, the patient interface comprising:
   a sealing structure having a seal surface adapted to contact skin on a patient's face;
   a plurality of capacitive sensors made of textile and weaved into material of the sealing structure, the plurality of capacitive sensors adapted to detect a range of different values of distance of proximity between the seal surface and the patient's face and to generate a sensor signal corresponding thereto;
   a processor configured to determine a sealing condition between the sealing structure and the patient based on the values of distance of proximity of the generated sensor signal; and
   a plurality of resistors for the plurality of capacitive sensors and the processor, the plurality of resistors providing a plurality of different sensitivities for the plurality of capacitive sensors for detecting different distances of proximity between the seal surface and the patient's face.

2. The patient interface of claim 1, wherein at least one capacitive sensor of the plurality of capacitive sensors is weaved into the sealing structure using conductive thread.

3. The patient interface of claim 1, wherein the sealing structure and at least one capacitive sensor of the plurality of capacitive sensors form a complete textile mask.

4. The patient interface of claim 1, wherein at least one capacitive sensor of the plurality of capacitive sensors is weaved into the seal surface of the sealing structure.

5. The patient interface of claim 4, wherein the seal surface of the sealing structure comprises a cushion.

6. The patient interface of claim 1, wherein at least one capacitive sensor of the plurality of capacitive sensors includes one or more conductive paths to transmit information detected by the at least one capacitive sensor to the processor.

7. The patient interface of claim 1, wherein the determined sealing condition includes any one of (1) an unintentional leak, (2) an adequate contact, and (3) an inadequate contact between the sealing structure and the patient's face.

8. The patient interface of claim 1, wherein the processor is further configured to determine a type of sealing condition from a plurality of sealing conditions based on a signal strength of the generated sensor signal.

9. The patient interface of claim 8, wherein the processor determines that a touch has occurred or an excessive force has been applied against the patient's face when the signal strength of the generated sensor signal exceeds a predetermined threshold.

10. The patient interface of claim 9, wherein the processor determines that no touch or an inferior touch has occurred when the signal strength does not exceed the predetermined threshold.

11. The patient interface of claim 1, wherein the plurality of capacitive sensors are weaved into material of the sealing structure at different locations on the sealing structure.

12. The patient interface of claim 11, wherein the processor is configured to determine a type of sealing condition from a plurality of sealing conditions at each sensor location.

13. The patient interface of claim 1, further comprising a positioning structure adapted to secure the sealing structure to the patient's face.

14. The patient interface of claim 13, wherein the processor is further configured to generate one or more signals to adjust at least one of the sealing structure and the positioning structure to maintain the sealing structure in sealing contact with the patient based on the determined sealing condition.

15. The patient interface of claim 14, wherein the processor is further configured to adjust at least one of the sealing structure and the positioning structure based on the determined sealing condition by activating at least one adjustment component of the patient interface.

16. The patient interface of claim 15, wherein the at least one adjustment component comprises a shape memory alloy.

17. The patient interface of claim 16, wherein the shape memory alloy is nitinol.

18. The patient interface of claim 16, wherein the positioning structure comprises headgear and the at least one adjustment component adjusts tension in a headgear strap of the headgear.

19. The patient interface of claim 16, wherein the at least one adjustment component is included in the sealing structure.

20. The patient interface of claim 15, wherein the at least one adjustment component comprises a shape-changing material that is included in the sealing structure, wherein the shape-changing material is configured to change the shape or geometry of the sealing structure in response to a temperature change.

21. The patient interface of claim 15, further comprising a prediction system configured to predict whether a loss of seal between the seal surface and the patient's face is likely to occur based on the generated sensor signal.

22. The patient interface of claim 21, wherein the prediction system is configured to activate the at least one adjustment component when it is determined that a loss of seal is likely to occur.

23. The patient interface of claim 1, wherein at least one capacitive sensor of the plurality of capacitive sensors generates a fluctuating sensor signal indicative of an unstable contact between the sealing structure and the patient's face.

24. The patient interface of claim 1, wherein the processor is configured to control a flow generator to supply the flow of breathable gas to the patient based on the determined sealing condition.

25. The patient interface of claim 24, wherein the processor instructs the flow generator to start supplying the flow of breathable gas to the patient when the sealing structure is in sealing contact with the patient.

26. The patient interface of claim 24, wherein the processor instructs the flow generator to stop supplying the flow of breathable gas to the patient when the sealing structure is not in sealing contact with the patient.

27. The patient interface of claim 1, wherein the processor is configured to detect at least one state from a plurality of states by evaluation of the generated sensor signal, the plurality of states comprising a first state indicating that the patient interface is being worn, a second state indicating that the patient interface is ill-fit, and a third state indicating that the patient interface is not being worn.

28. The patient interface of claim 27, wherein the processor is configured to output an indication of the detected state.

29. The patient interface of claim 28, wherein the processor is configured to determine the first state when the processor determines the seal surface is contacting the patient's face, the second state when the processor determines that at least a portion of the seal surface is close to the patient's face and not contacting the patient's face, and the third state when the processor determines that the seal surface is not contacting the patient's face and not close to the patient's face.

* * * * *